(12) United States Patent
Semple et al.

(10) Patent No.: US 9,403,786 B2
(45) Date of Patent: Aug. 2, 2016

(54) ANTI-INFLAMMATORY COMPOUNDS

(75) Inventors: Susan J. Semple, Mylor (AU); Bradley S. Simpson, Highbury (AU); Ross Allan McKinnon, Eden Hills (AU); David Claudie, Cairns (AU); Jacobus P. Gerber, Eden Valley (AU); Jiping Wang, Felixstow (AU); George Moreton, Sr., Cairns (AU)

(73) Assignees: University of South Australia, Adelaide, S.A. (AU); Chuulangun Aboriginal Corporation, Queensland (AU)

( * ) Notice: Subject to any disclaimer, the term of this patent is extended or adjusted under 35 U.S.C. 154(b) by 1120 days.

(21) Appl. No.: 13/509,194

(22) PCT Filed: Nov. 10, 2010

(86) PCT No.: PCT/AU2010/001502
§ 371 (c)(1),
(2), (4) Date: Aug. 6, 2012

(87) PCT Pub. No.: WO2011/057332
PCT Pub. Date: May 19, 2011

(65) Prior Publication Data
US 2013/0053437 A1 Feb. 28, 2013

(30) Foreign Application Priority Data
Nov. 10, 2009 (AU) ................................ 2009905498

(51) Int. Cl.
*C07D 307/42* (2006.01)
*C07D 307/54* (2006.01)

(52) U.S. Cl.
CPC ............ *C07D 307/42* (2013.01); *C07D 307/54* (2013.01)

(58) Field of Classification Search
None
See application file for complete search history.

(56) References Cited

U.S. PATENT DOCUMENTS 6,143,303 A   11/2000   Janakiram et al.

FOREIGN PATENT DOCUMENTS

WO   2011/057327 A1   5/2011

OTHER PUBLICATIONS

Banker, Gilbert. Modern Pharmaceutics 3rd ed. Marcel Dekker, Inc. New York, 1996.*
Nordqvist, Christian. "Inflammation: Causes, Symptoms and Treatment." Medical News Today. MediLexicon, Intl., Sep. 16, 2015. Web. <http://www.medicalnewstoday.com/articles/248423.php>.*
Hardard Health Publications: Harvard Medical School "Foods that fight inflammation". Jul. 1, 2014. Web <http://www.health.harvard.edu/staying-healthy/foods-that-fight-inflammation>.*
Lee, D.Y.W. et al., New Neoclerodane Diterpenoids Isolated From the Leaves of Salvia Divinorum and Their Binding Affinities for Human k Opioid Receptors, Bioorganic & Medicinal Chemistry 13, 5635-5639 (2005).
Bigham, A.K. et al., Divinatorins A-C, New Neoclerodane Diterpenoids from the Controlled Sage Salvia Divinorum, J. Nat. Prod. 66, 1242-1244 (2003).
Medana, C. et al., Determination of Salvinorins and Divinatorins in Salvia Divinorum Leaves by Liquid Chromatography/Multistage Mass Spectrometry, Rapid Communications in Mass Spectrometry 20, 131-136 (2006).
Venkateswarlu, K. et al., A Benzofuranoid and Two Clerodane Diterpenoids from Pulicaria Wightlana, Helvetica Chimica Acta 91: 2081-2088 (2008).
Jefferies, P.R. et al., Structure Elucidation of Some Ent-Clerodane Diterpenes From Dodonaea Boroniaefolia and Cyanostegia Angustifolia, Australian Journal of Chemistry 26 (10), 2199-2211 (1973).
Jefferies, P.R. et al., Diterpenes of the Cascarillin Group From Dodonaea SPP., Tetrahedron Letters (48) 4777-4782 (1967).
Payne, T.G. et al., The Chemistry of Dodonaea SPP-IV. Diterpene and Flavonoid Components of D. attenuata, Tetrahedron 29, 2575-2583 (1973).
Anis, I., et al., Thrombin Inhibitory Constituents from Duranta Repens, Helvetica Chimica Acta, vol. 84, 649-655, (2001).
Bigham, A.K. et al., Divinatorins A-C, New Neoclerodane Diterpenoids from the Controlled Sage Salvia divinorum, Journal of Natural Products, vol. 66, (9), 1242-1244, (2003).
Jolad, S.D. et al., Diterpenoids of Conyza Coulteri, Phytochemistry, vol. 27 (4), 1211-1212 (1988).
Lee, D.Y.W. et al., New Neoclerodane Diterpenoids Isolated from the Leaves of Salvia Divinorum and their Binding Affinities for Human Kappa Opioid Receptors, Bioorganic & Medicinal Chemistry, vol. 13 (19), 5635-5639 (2005).
Munro, T.A. et al., Autoxidation of Salvinorin a Under Basic Conditions, The Journal of Organic Chemistry, vol. 70, (24) 10057-10061, (2005).
Pandey, U.C. et al., Stereochemistry of Strictic Acid and Related Furano-Diterpenes from Conyza Japonica and Grangea Maderaspatana, Phytochemistry, vol. 23 (2), 391-397, (1984).
Simpson, B.S., Chemical and Pharmacological Investigation of Dodonaea Polyandra, Ph.D. Thesis, Division of Health Science, School of Pharmacy and Medical Sciences, University of South Australia (2011).
Wilson, S.R. et al., The Chemistry of the Euphorbiaceae. A New Diterpene from Croton Californicus, Journal of the American Chemical Society, vol. 98 (12), 3669-3674, (1976).
Zdero, C. et al., Clerodane Derivatives From Diplostephium, Phytochemistry, vol. 31 (1), 213-216, (1992).

* cited by examiner

*Primary Examiner* — Golam M M Shameem
*Assistant Examiner* — Laura Daniel
(74) *Attorney, Agent, or Firm* — Olson & Cepuritis, Ltd.

(57) ABSTRACT

New clerodane compounds isolated from plant material from *Dodonaea polyandra* are disclosed. The compounds have anti-inflammatory activity. Pharmaceutical and cosmetic compositions containing the compounds, as well as methods of treating inflammation using the compounds, are also disclosed.

17 Claims, 16 Drawing Sheets

Figure 1

| Extract | % inhibition (mean ± SEM) (p-value) | | | | Yield (%) |
|---|---|---|---|---|---|
| | Maximum | | Average | | |
| n-hexane (n=4) | 46.4 ± 6.2* | < 0.001 | 57.8 ± 4.4* | < 0.001 | 1.2 |
| 80% ethanol(n=4) | 44.0 ± 2.8* | < 0.001 | 61.8 ± 4.3* | < 0.001 | 17.7 |
| Methylene chloride/methanol (1:1) (n=4) | 36.2 ± 5.1* | < 0.001 | 58.9 ± 4.0* | < 0.001 | 22.3 |
| 80% ethanol (sequential) (n=4) | 25.9 ± 4.2* | < 0.001 | 44.7 ± 8.1* | < 0.001 | 15.4 |
| Methylene chloride/methanol (1:1) (sequential) (n=4) | 44.0 ± 2.3* | 0.008 | 60.8 ± 2.9* | < 0.001 | 14.1 |
| Hydrocortisone (2 mg) (n=2) | 30.9 ± 1.4* | 0.006 | 44.9 ± 11.0* | 0.001 | n/a |

*statistically significant relative to TPA control at $\alpha = 0.05$

Figure 5

| Extract/concentration | % inhibition (mean ± SEM) (p-value) | | | |
|---|---|---|---|---|
| | Maximum | | Average | |
| Stem 0.4 mg/ear (n=3) | 52.9 ± 11.9 | 0.074 | 52.3 ± 11.7 | 0.064 |
| Stem 0.04 mg/ear (n=3) | 9.6 ± 9.9 | 0.674 | 15.0 ± 3.7 | 0.562 |
| Stem 0.004 mg/ear (n=3) | 59.1 ± 8.5* | 0.047 | 62.1 ± 14.8* | 0.030 |

*statistically significant relative to croton oil control at $\alpha = 0.05$

Compound C

Compound E

Compound F

Compound H

Figure 13

| Semi-pure fraction | % inhibition (mean ± SEM) (p-value) | | | |
|---|---|---|---|---|
| | Maximum | | Average | |
| LH1 (n=3) | 46.3 ± 7.1* | 0.028 | 37.6 ± 5.5* | 0.025 |
| LH2 (n=3) | 75.5 ± 6.5* | <0.001 | 42.1 ± 11.0* | 0.010 |
| LH3 (n=3) | 27.4 ± 5.6 | 0.310 | 27.4 ± 8.8 | 0.147 |
| LH4 (n=3) | 41.0 ± 8.9 | 0.062 | 27.4 ± 2.7 | 0.147 |
| LH5 (n=3) | 29.5 ± 9.5 | 0.252 | 29.1 ± 8.0 | 0.113 |
| LH6 (n=3) | 11.2 ± 6.4 | 0.824 | 21.2 ± 1.2 | 0.335 |
| LH7 (n=3) | 25.4 ± 12.5 | 0.372 | 4.1 ± 6.6 | 0.933 |
| LH8 (n=3) | 15.9 ± 11.1 | 0.693 | 16.3 ± 7.0 | 0.541 |
| LH9 (n=3) | 32.1 ± 15.1 | 0.190 | 27.3 ± 13.0 | 0.149 |
| LH10 (n=3) | 28.9 ± 15.0 | 0.268 | 14.4 ± 14.7 | 0.620 |
| LH11 (n=3) | 64.0 ± 27.4* | 0.001 | 41.7 ± 19.5* | 0.011 |
| LH12 (n=3) | 60.0 ± 7.8* | 0.003 | 37.6 ± 2.5* | 0.025 |
| LH13 (n=3) | 51.0 ± 26.6* | 0.013 | 35.6 ± 16.3* | 0.036 |

*statistically significant relative to TPA control at $\alpha = 0.05$

ANTI-INFLAMMATORY COMPOUNDS

FIELD

The present invention relates to compounds, and pharmaceutical compositions containing them, that may be used in the treatment of inflammation. The present invention also relates to methods for treating inflammation using those compounds.

INCORPORATION BY REFERENCE

This patent application claims priority from Australian Provisional Patent Application 2009905498, titled "ANTI-INFLAMMATORY COMPOUNDS", and filed on 10 Nov., 2009, the entire contents of which are hereby incorporated by reference.

BACKGROUND

Inflammation is a complex biological process that occurs in response to stimuli including, for example, infection, damage to cells and/or tissue, irritants, etc. While inflammation is vital for healing and combating infection, abnormal or excessive inflammation can adversely affect the health, comfort and/or mobility of a subject.

A wide range of anti-inflammatory agents are known including steroids (such as glucocorticoids) and non-steroidal anti-inflammatory drugs (such as aspirin, ibuprofen, naproxen, etc). However, these drugs may be ineffective at treating some inflammatory conditions and/or may be associated with adverse side effects.

For example, some current anti-inflammatory agents have adverse side effects which include any one or more of gastrointestinal tract damage, renal damage, photosensitivity, hepatic stimulation, headaches, dizziness, Crushing's syndrome, hypertension, hypokalemia, hypernatremia, etc. Furthermore, due to adverse reactions some anti-inflammatory agents may not be suitable for some subjects including, for example, pregnant subjects and subjects with an inflammatory bowel disease. Adverse side-effects of anti-inflammatory agents may result from topical, oral or other forms of administration.

Due to the limitations of many current anti-inflammatory drugs, there is a continual need to develop new anti-inflammatory agents. Identification and isolation or synthesis of compounds with anti-inflammatory properties is desirable.

Reference to any prior art in this specification is not, and should not be taken as, an acknowledgment or any form of suggestion that this prior art forms part of the common general knowledge in any country.

SUMMARY

The present invention arises from the discovery of a range of novel diterpene compounds that show anti-inflammatory activity in a mouse ear oedema assay.

In one aspect, the present invention provides a compound of formula (I)

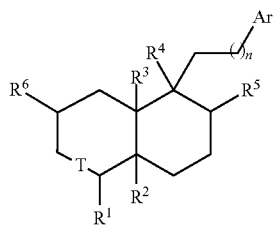

or a pharmaceutically acceptable salt or prodrug thereof, wherein:

T is a single bond or a double bond;

$R^1$ is selected from the group consisting of: $COOR^7$, $CONR^7R^8$, $COSR^7$, $COR^7$, $SO_3H$, $SO^2NR^7R^8$, $SO_2R^7$, $SONR_7R^8$, and $SOR^7$;

$R^2$, $R^3$, and $R^4$ are each independently selected from the group consisting of: H, optionally substituted C1-C12 alkyl, and optionally substituted C2-C12 alkenyl;

$R^5$ and $R^6$ are each independently selected from the group consisting of: H, OH, optionally substituted C1-C12 alkyl, =O ($R^5$ and/or $R^6$ together with the hydrogen attached to the carbon atom to which they are attached are replaced by the =O moiety), $(CH_2)mOC(O)R^9$, C1-C12 oxyalkyl, C1-C12 alkyloxy, C2-C12 oxyalkenyl, and C2-C12 alkenyloxy, provided at least one of $R^5$ and $R^6$ is $(CH_2)mOC(O)R^9$ and when $R^5$ is methyl and $R^6$ is $OC(O)R^9$, $R^9$ is not $CH_3$;

$R^7$ and $R^8$ are each independently selected from the group consisting of: H, optionally substituted C1-C12 alkyl, optionally substituted C2-C12 alkenyl, optionally substituted C2-C12 alkynyl, optionally substituted C1-C10 heteroalkyl, optionally substituted C3-C12 cycloalkyl, optionally substituted C3-C12 cycloalkenyl, optionally substituted C1-C12 heterocycloalkyl, optionally substituted C1-C12 heterocycloalkenyl, optionally substituted C6-C18 aryl, and optionally substituted C1-C18 heteroaryl;

$R^9$ is selected from the group consisting of: optionally substituted C1-C12 alkyl, optionally substituted C2-C12 alkenyl, optionally substituted C2-C12 alkynyl, optionally substituted C1-C10 heteroalkyl, optionally substituted C3-C12 cycloalkyl, optionally substituted C3-C12 cycloalkenyl, optionally substituted C1-C12 heterocycloalkyl, optionally substituted C1-C12 heterocycloalkenyl, optionally substituted C6-C18 aryl, and optionally substituted C1-C18 heteroaryl;

Ar is an optionally substituted aryl group; and m and n are integers each of which is selected from the group consisting of 0, 1, 2, 3, and 4.

As with any group of structurally related compounds which possess a particular utility, certain embodiments of variables of the compounds of formula (I), are particularly useful in their end use application.

In some embodiments the compound has either formula (Ia) or formula (Ib):

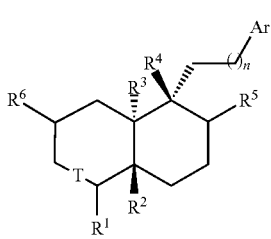

(Ia)

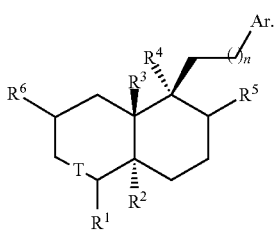

(Ib)

In various embodiments $R^9$ is optionally substituted C6-C18 aryl. In some embodiments $R^9$ is phenyl. In some embodiments only one of $R^5$ and $R^6$ is $(CH_2)mOC(O)R^9$. In some embodiments m is selected from the group consisting of 0 and 1.

In some embodiments T is a double bond.

In some embodiments n is 1.

In various embodiments Ar is selected from the group consisting of: optionally substituted furan, optionally substituted thiophene, optionally substituted pyrrole, optionally substituted phenyl, and optionally substituted pyridine. In some embodiments Ar is furan.

In various embodiments $R^1$ is $COOR^7$. In some embodiments $R^7$ is H.

In some embodiments $R^2$ is optionally substituted C1-C12 alkyl.

In some embodiments $R^2$ is methyl.

In some embodiments $R^3$ is H.

In various embodiments $R^4$ is optionally substituted C1-C12 alkyl. In some embodiments $R^4$ is methyl.

From the foregoing, it will be evident that in some embodiments the present invention provides compounds of formula (II):

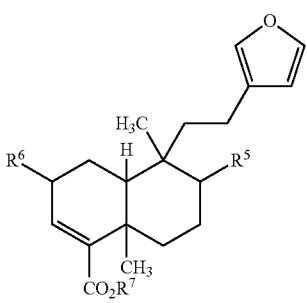

(II)

or a pharmaceutically acceptable salt or prodrug thereof; wherein $R^5$, $R^6$, and $R^7$ are as defined above.

In various embodiments $R^5$ is $(CH_2)mOC(O)R^9$ and $R^6$ is selected from the group consisting of H and OH.

In various embodiments $R^6$ is $(CH_2)mOC(O)R^9$ and $R^5$ is optionally substituted C1-C12 alkyl. In some embodiments $R^5$ is methyl.

In another aspect, the present invention provides a composition comprising a compound as described herein. The composition may be a pharmaceutical composition or a cosmetic composition.

In a further aspect, the present invention provides a method of treating or preventing inflammation in a subject, the method comprising administering to the subject a therapeutically effective amount of a compound as described herein.

In another aspect, the present invention provides a method of treating or preventing inflammation in a subject, the method comprising administering to the subject a therapeutically effective amount of a composition as described herein.

In another aspect, the present invention provides a method of treating a disease or condition characterised by or associated with inflammation, the method comprising administering to a subject in need of such treatment a therapeutically effective amount of a compound as described herein.

In a further aspect, the present invention provides a method of treating a disease or condition characterised by or associated with inflammation, the method comprising administering to a subject in need of such treatment a therapeutically effective amount of a composition as described herein.

In various embodiments the subject is a mammal. In some embodiments the subject is a human.

The present invention also provides for the use of a compound as described herein in the treatment of a disease or condition characterised by or associated with inflammation.

Furthermore, the present invention provides for the use of a compound as described herein in the preparation of a medicament for the treatment or prevention of inflammation.

DESCRIPTION OF EXEMPLARY EMBODIMENTS

It is to be understood that the following description is for the purpose of describing particular embodiments only, and is not intended to be limiting with respect to the above description.

In this specification a number of terms are used which are well known to a skilled addressee. Nevertheless for the purposes of clarity a number of terms will be defined.

The term "unsubstituted" as used throughout the specification means that there is no substituent or that the only substituents are hydrogen.

The term "optionally substituted" as used throughout the specification denotes that the group may or may not be further substituted or fused (so as to form a condensed polycyclic system), with one or more non-hydrogen substituent groups. In certain embodiments the substituent groups are one or more groups independently selected from the group consisting of halogen, =O, =S, —CN, —NO$_2$, —CF$_3$, —OCF$_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, cycloalkylalkyl, heterocycloalkylalkyl, heteroarylalkyl, arylalkyl, cycloalkylalkenyl, heterocycloalkylalkenyl, arylalkenyl, heteroarylalkenyl, cycloalkylheteroalkyl, heterocycloalkylheteroalkyl, arylheteroalkyl, heteroarylheteroalkyl, hydroxy, hydroxyalkyl, alkyloxy, alkyloxyalkyl, alkyloxycycloalkyl, alkyloxyheterocycloalkyl, alkyloxyaryl, alkyloxyheteroaryl, alkyloxycarbonyl, alkylaminocarbonyl, alkenyloxy, alkynyloxy, cycloalkyloxy, cycloalkenyloxy, heterocycloalkyloxy, heterocycloalkenyloxy, aryloxy, phenoxy, benzyloxy, heteroaryloxy, arylalkyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, alkylsulfinyl, arylsulfinyl, aminosulfinylaminoalkyl, —C(=O)

OH, —C(=O)R$^a$, —C(=O)OR$^a$, C(=O)NR$^a$R$^b$, C(=NOH)R$^a$, C(=NR$^a$)NR$^b$R$^c$, NR$^a$R$^b$, NR$^a$C(=O)R$^b$, NR$^a$C(=O)OR$^b$, NR$^a$C(=O)NR$^b$R$^c$, NR$^a$C(=NR$^b$)NR$^c$R$^d$, NR$^a$SO$_2$R$^b$, —SR$^a$, SO$_2$NR$^a$R$^b$, —OR$^a$, OC(=O)NR$^a$R$^b$, OC(=O)R$^a$ and acyl,
wherein R$^a$, R$^b$, R$^c$ and R$^d$ are each independently selected from the group consisting of H, C$_1$-C$_{12}$ alkyl, C$_1$-C$_{12}$haloalkyl, C$_2$-C$_{12}$alkenyl, C$_2$-C$_{12}$alkynyl, C$_2$-C$_{10}$ heteroalkyl, C$_3$-C$_{12}$cycloalkyl, C$_3$-C$_{12}$cycloalkenyl, C$_2$-C$_{12}$heterocycloalkyl, C$_2$-C$_{12}$ heterocycloalkenyl, C$_6$-C$_{18}$aryl, C$_1$-C$_{18}$heteroaryl, and acyl, or any two or more of R$^a$, R$^b$, R$^c$ and R$^d$, when taken together with the atoms to which they are attached form a heterocyclic ring system with 3 to 12 ring atoms.

In some embodiments each optional substituent is independently selected from the group consisting of: halogen, =O, =S, —CN, —NO$_2$, —CF$_3$, —OCF$_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, hydroxy, hydroxyalkyl, alkyloxy, alkyloxyalkyl, alkyloxyaryl, alkyloxyheteroaryl, alkenyloxy, alkynyloxy, cycloalkyloxy, cycloalkenyloxy, heterocycloalkyloxy, heterocycloalkenyloxy, aryloxy, heteroaryloxy, arylalkyl, heteroarylalkyl, arylalkyloxy, amino, alkylamino, acylamino, aminoalkyl, arylamino, sulfonyl, alkylsulfonyl, arylsulfonyl, aminosulfonyl, aminoalkyl, —COOH, —SH, and acyl.

Examples of particularly suitable optional substituents include F, Cl, Br, I, CH$_3$, CH$_2$CH$_3$, OH, OCH$_3$, CF$_3$, OCF$_3$, NO$_2$, NH$_2$, and CN.

In the definitions of a number of substituents below it is stated that "the group may be a terminal group or a bridging group". This is intended to signify that the use of the term is intended to encompass the situation where the group is a linker between two other portions of the molecule as well as where it is a terminal moiety. Using the term alkyl as an example, some publications would use the term "alkylene" for a bridging group and hence in these other publications there is a distinction between the terms "alkyl" (terminal group) and "alkylene" (bridging group). In the present application no such distinction is made and most groups may be either a bridging group or a terminal group.

"Alkenyl" as a group or part of a group denotes an aliphatic hydrocarbon group containing at least one carbon-carbon double bond and which may be straight or branched preferably having 2-12 carbon atoms, more preferably 2-10 carbon atoms, most preferably 2-6 carbon atoms, in the normal chain. The group may contain a plurality of double bonds in the normal chain and the orientation about each is independently E or Z. Exemplary alkenyl groups include, but are not limited to, ethenyl, propenyl, butenyl, pentenyl, hexenyl, heptenyl, octenyl and nonenyl. The group may be a terminal group or a bridging group.

"Alkenyloxy" refers to an alkenyl-O— group in which alkenyl is as defined herein. Preferred alkenyloxy groups are C$_1$-C$_6$ alkenyloxy groups. The group may be a terminal group or a bridging group. If the group is a terminal group it is bonded to the remainder of the molecule through the oxygen atom.

"Alkyl" as a group or part of a group refers to a straight or branched aliphatic hydrocarbon group, preferably a C$_1$-C$_{12}$ alkyl, more preferably a C$_1$-C$_{10}$ alkyl, most preferably C$_1$-C$_6$ unless otherwise noted. Examples of suitable straight and branched C$_1$-C$_6$ alkyl substituents include methyl, ethyl, n-propyl, 2-propyl, n-butyl, sec-butyl, t-butyl, hexyl, and the like. The group may be a terminal group or a bridging group.

"Alkyloxy" refers to an alkyl-O— group in which alkyl is as defined herein. Preferably the alkyloxy is a C$_1$-C$_6$alkyloxy. Examples include, but are not limited to, methoxy and ethoxy. The group may be a terminal group or a bridging group.

"Alkynyl" as a group or part of a group means an aliphatic hydrocarbon group containing a carbon-carbon triple bond and which may be straight or branched preferably having from 2-12 carbon atoms, more preferably 2-10 carbon atoms, more preferably 2-6 carbon atoms in the normal chain. Exemplary structures include, but are not limited to, ethynyl and propynyl. The group may be a terminal group or a bridging group.

"Aryl" as a group or part of a group denotes (i) an optionally substituted monocyclic, or fused polycyclic, aromatic carbocycle (ring structure having ring atoms that are all carbon) preferably having from 5 to 12 atoms per ring. Examples of aryl groups include phenyl, naphthyl, and the like; (ii) an optionally substituted partially saturated bicyclic aromatic carbocyclic moiety in which a phenyl and a C$_{5-7}$ cycloalkyl or C$_{5-7}$ cycloalkenyl group are fused together to form a cyclic structure, such as tetrahydronaphthyl, indenyl or indanyl. The group may be a terminal group or a bridging group. Typically an aryl group is a C$_6$-C$_{18}$ aryl group.

"Cycloalkenyl" means a non-aromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl or cycloheptenyl. The cycloalkenyl group may be substituted by one or more substituent groups. A cycloalkenyl group typically is a C$_3$-C$_{12}$ alkenyl group. The group may be a terminal group or a bridging group.

"Cycloalkyl" refers to a saturated monocyclic or fused or spiro polycyclic, carbocycle preferably containing from 3 to 9 carbons per ring, such as cyclopropyl, cyclobutyl, cyclopentyl, cyclohexyl and the like, unless otherwise specified. It includes monocyclic systems such as cyclopropyl and cyclohexyl, bicyclic systems such as decalin, and polycyclic systems such as adamantane. A cycloalkyl group typically is a C$_3$-C$_{12}$ alkyl group. The group may be a terminal group or a bridging group.

"Halogen" represents chlorine, fluorine, bromine or iodine.

"Heteroalkyl" refers to a straight- or branched-chain alkyl group preferably having from 2 to 12 carbons, more preferably 2 to 6 carbons in the chain, in which one or more of the carbon atoms (and any associated hydrogen atoms) are each independently replaced by a heteroatomic group selected from S, O, P and NR' where R' is selected from the group consisting of H, optionally substituted C$_1$-C$_{12}$alkyl, optionally substituted C$_3$-C$_{12}$cycloalkyl, optionally substituted C$_6$-C$_{18}$aryl, and optionally substituted C$_1$-C$_{18}$heteroaryl. Exemplary heteroalkyls include alkyl ethers, secondary and tertiary alkyl amines, amides, alkyl sulfides, and the like. Examples of heteroalkyl also include hydroxyC$_1$-C$_6$alkyl, C$_1$-C$_6$alkyloxyC$_1$-C$_6$alkyl, aminoC$_1$-C$_6$alkyl, C$_1$-C$_6$alkylaminoC$_1$-C$_6$alkyl, and di(C$_1$-C$_6$alkyl)aminoC$_1$-C$_6$alkyl. The group may be a terminal group or a bridging group.

"Heteroaryl" either alone or part of a group refers to groups containing an aromatic ring (preferably a 5 or 6 membered aromatic ring) having one or more heteroatoms as ring atoms in the aromatic ring with the remainder of the ring atoms being carbon atoms. Suitable heteroatoms include nitrogen, oxygen and sulphur. Examples of heteroaryl include thiophene, benzothiophene, benzofuran, benzimidazole, benzoxazole, benzothiazole, benzisothiazole, naphtho[2,3-b] thiophene, furan, isoindolizine, xantholene, phenoxatine, pyrrole, imidazole, pyrazole, pyridine, pyrazine, pyrimidine, pyridazine, tetrazole, indole, isoindole, 1H-indazole, purine, quinoline, isoquinoline, phthalazine, naphthyridine, quinoxaline, cinnoline, carbazole, phenanthridine, acridine, phenazine, thiazole, isothiazole, phenothiazine, oxazole, isooxazole, furazane, phenoxazine, 2-, 3- or 4-pyridyl, 2-, 3-, 4-, 5-, or 8-quinolyl, 1-, 3-, 4-, or 5-isoquinolinyl 1-, 2-, or 3-indolyl, and 2-, or 3-thienyl. A heteroaryl group is typically a $C_1$-$C_{18}$ heteroaryl group. The group may be a terminal group or a bridging group.

"Heterocycloalkenyl" refers to a heterocycloalkyl group as defined herein but containing at least one double bond. A heterocycloalkenyl group typically is a $C_2$-$C_{12}$ heterocycloalkenyl group. The group may be a terminal group or a bridging group.

"Heterocycloalkyl" refers to a saturated monocyclic, bicyclic, or polycyclic ring containing at least one heteroatom selected from nitrogen, sulfur, oxygen, preferably from 1 to 3 heteroatoms in at least one ring. Each ring is preferably from 3 to 10 membered, more preferably 4 to 7 membered. Examples of suitable heterocycloalkyl substituents include pyrrolidyl, tetrahydrofuryl, tetrahydrothiofuranyl, piperidyl, piperazyl, tetrahydropyranyl, morphilino, 1,3-diazapane, 1,4-diazapane, 1,4-oxazepane, and 1,4-oxathiapane. A heterocycloalkyl group typically is a $C_2$-$C_{12}$ heterocycloalkyl group. The group may be a terminal group or a bridging group.

"Lower alkyl" as a group means unless otherwise specified, an aliphatic hydrocarbon group which may be straight or branched having 1 to 6 carbon atoms in the chain, more preferably 1 to 4 carbons such as methyl, ethyl, propyl (n-propyl or isopropyl) or butyl (n-butyl, isobutyl or tertiary-butyl). The group may be a terminal group or a bridging group.

"Oxyalkenyl" refers to an $R^a$O-alkenyl-group in which alkenyl and $R^a$ are as defined herein. Preferably the oxyalkenyl is a $C_2$-$C_6$ oxyalkenyl, namely $R^a$O—C2-C6alkenyl-. Examples include $R^a$O—CH=CH—, $R^a$O—CH$_2$CH=CH—, $R^a$O—CH=CHCH$_2$—. The group may be a terminal group or a bridging group.

"Oxyalkyl" refers to an $R^a$O-alkyl-group in which alkyl and $R^a$ are as defined herein. Preferably the oxyalkyl is a $C_1$-$C_6$ oxyalkyl, namely $R^a$O—C1-C6alkyl-. Examples include $R^a$O—CH$_2$—, $R^a$O—CH$_2$CH$_2$—, $R^a$O—CH$_2$CH$_2$CH$_2$—. The group may be a terminal group or a bridging group It is understood that included in the family of compounds of Formula (I) are isomeric forms including diastereoisomers, enantiomers, tautomers, and geometrical isomers in "E" or "Z" configurational isomer or a mixture of E and Z isomers. It is also understood that some isomeric forms such as diastereomers, enantiomers, and geometrical isomers can be separated by physical and/or chemical methods and by those skilled in the art.

Some of the compounds of the disclosed embodiments may exist as single stereoisomers, racemates, and/or mixtures of enantiomers and/or diastereomers. All such single stereoisomers, racemates and mixtures thereof, are intended to be within the scope of the subject matter described and claimed.

Additionally, formula (I) is intended to cover, where applicable, solvated as well as unsolvated forms of the compounds. Thus, each formula includes compounds having the indicated structure, including the hydrated as well as the non-hydrated forms.

The term "pharmaceutically acceptable salts" refers to salts that retain the desired biological activity of the above-identified compounds, and include pharmaceutically acceptable acid addition salts and base addition salts. Suitable pharmaceutically acceptable acid addition salts of compounds of formula (I) may be prepared from an inorganic base or from an organic base. Information on pharmaceutically acceptable salts can be found in Remington's Pharmaceutical Sciences, 19th Edition, Mack Publishing Co., Easton, Pa. 1995. In the case of agents that are solids, it is understood by those skilled in the art that the inventive compounds, agents and salts may exist in different crystalline or polymorphic forms, all of which are intended to be within the scope of the present invention and specified formulae.

The term "prodrug" means a compound that undergoes conversion to a compound of formula (I) within a biological system, usually by metabolic means (e.g. by hydrolysis, reduction or oxidation). For example an ester prodrug of a compound of formula (I) containing a hydroxyl group may be convertible by hydrolysis in vivo to the parent molecule. Suitable esters of compounds of formula (I) containing a hydroxyl group, are for example acetates, citrates, lactates, tartrates, malonates, oxalates, salicylates, propionates, succinates, fumarates, maleates, methylene-bis-β-hydroxynaphthoates, gestisates, isethionates, di-p-toluoyltartrates, methanesulphonates, ethanesulphonates, benzenesulphonates, p-toluenesulphonates, cyclohexylsulphamates and quinates. As another example an ester prodrug of a compound of formula (I) containing a carboxy group may be convertible by hydrolysis in vivo to the parent molecule. (Examples of ester prodrugs are those described by F. J. Leinweber, Drug Metab. Res., 18:379, 1987).

The term "therapeutically effective amount" or "effective amount" is an amount sufficient to effect beneficial or desired clinical results. An effective amount can be administered in one or more administrations. An effective amount is typically sufficient to palliate, ameliorate, stabilize, reverse, slow or delay the progression of the disease state.

The term "inflammation" as used herein is intended to mean the process by which a subject's immune system coordinates a response to tissue damage, infection, antigenic challenge, etc. Inflammation may be associated with any one or more of an increased blood supply to the tissue, increased capillary permeability in the tissue and increased leukocyte migration to the tissue.

The term "treating" as used herein in relation to inflammation in a subject is intended to mean that the compound or pharmaceutical composition reduces or abrogates the symptoms and/or cause of the inflammation.

The term "preventing" as used herein in relation to inflammation in a subject is intended to mean that the compound or pharmaceutical composition substantially prevents an inflammatory response and/or reduces the symptoms of the inflammatory response that would otherwise occur had the subject not been treated with the compound or pharmaceutical composition.

A first aspect of the invention provides a compound of formula (I)

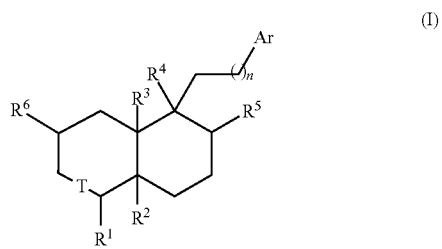

or a pharmaceutically acceptable salt or prodrug thereof, wherein:

T is a single bond or a double bond;

$R^1$ is selected from the group consisting of: $COOR^7$, $CONR^7R^8$, $COSR^7$, $COR^7$, $SO_3H$, $SO^2NR^7R^8$, $SO_2R^7$, $SONR_7R^8$, and $SOR^7$;

$R^2$, $R^3$, and $R^4$ are each independently selected from the group consisting of: H, optionally substituted C1-C12 alkyl, and optionally substituted C2-C12 alkenyl;

$R^5$ and $R^6$ are each independently selected from the group consisting of: H, OH, optionally substituted C1-C12 alkyl, =O ($R^5$ and/or $R^6$ together with the hydrogen attached to the carbon atom to which they are attached are replaced by the =O moiety), $(CH_2)mOC(O)R^9$, C1-C12 oxyalkyl, C1-C12 alkyloxy, C2-C12 oxyalkenyl, and C2-C12 alkenyloxy, provided at least one of $R^5$ and $R^6$ is $(CH_2)mOC(O)R^9$ and when $R^5$ is methyl and $R^6$ is $OC(O)R^9$, $R^9$ is not $CH_3$;

$R^7$ and $R^8$ are each independently selected from the group consisting of: H, optionally substituted C1-C12 alkyl, optionally substituted C2-C12 alkenyl, optionally substituted C2-C12 alkynyl, optionally substituted C1-C10 heteroalkyl, optionally substituted C3-C12 cycloalkyl, optionally substituted C3-C12 cycloalkenyl, optionally substituted C1-C12 heterocycloalkyl, optionally substituted C1-C12 heterocycloalkenyl, optionally substituted C6-C18 aryl, and optionally substituted C1-C18 heteroaryl;

$R^9$ is selected from the group consisting of: optionally substituted C1-C12 alkyl, optionally substituted C2-C12 alkenyl, optionally substituted C2-C12 alkynyl, optionally substituted C1-C10 heteroalkyl, optionally substituted C3-C12 cycloalkyl, optionally substituted C3-C12 cycloalkenyl, optionally substituted C1-C12 heterocycloalkyl, optionally substituted C1-C12 heterocycloalkenyl, optionally substituted C6-C18 aryl, and optionally substituted C1-C18 heteroaryl;

Ar is an optionally substituted aryl group; and m and n are integers each of which is selected from the group consisting of 0, 1, 2, 3, and 4.

Specific compounds of the invention include the following:

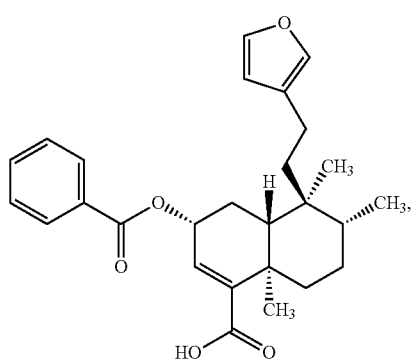

-continued

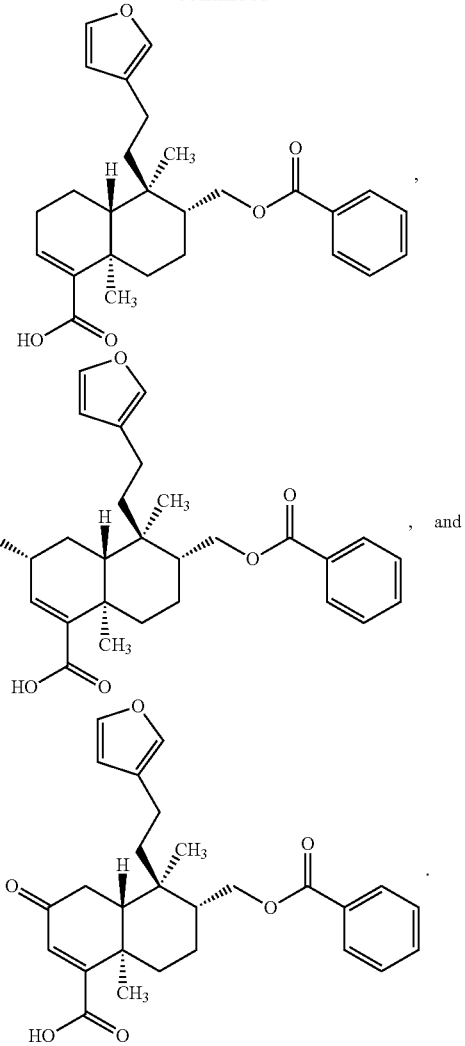

The compounds may be synthesised or they may be isolated from natural sources. The compounds used to prepare the compositions described herein may be at least 50% pure, 60% pure, 70% pure, 80% pure, 90% pure, 95% pure, 99% pure or 99.5% pure, as well as 100% pure. By "pure" it is meant that the compound of interest (i.e. the active compound) is free from other compounds. Similarly, the compounds may also be referred to as "isolated compounds" which means that the compound has been removed from its natural source and has been purified to some degree.

Methods of chemical synthesis are generally known in the art and the compounds of the various embodiments may be prepared employing techniques available in the art using starting materials that are readily available. The skilled person will recognise that known chemical reactions may be readily adapted to prepare compounds of the various embodiments. The synthesis of the compounds of the embodiments may be performed by modifications apparent to the skilled person, e.g. by appropriately protecting interfering groups, by changing to other suitable reagents known in the art, or by making routine modifications of reaction conditions. A list of suitable protecting groups in organic synthesis can be found in T. W. Greene's Protective Groups in Organic Synthesis, 3$^{rd}$ Edition, John Wiley & Sons, 1991. Alternatively, other reactions disclosed herein or known in the art will be recognised as having applicability for preparing other compounds of the various embodiments. Reagents useful for synthesising compounds may be obtained or prepared according to techniques known in the art. For example, approaches to synthesising the core decalin structure of the compounds of the present invention are provided in Ley et al. (*Chem. Soc., Chem. Commun.*, 1983, 503-505) and references cited therein.

Alternatively, the compound may be isolated from a natural source. For example, the compound may be isolated from a plant. In some embodiments, the compound may be isolated from a plant of the Dodonaeoideae subfamily.

Dodonaeoideae is a subfamily of flowing plants in the Sapindaceae family and includes, for example, the genera *Dodonaea* and *Koelreuteria*. The *Koelreuteria* genus comprises three species, namely, *Koelreuteria bipinnate, Koelreuteria elegans*, and *Koelreuteria paniculate*.

In some embodiments, the plant may be of the *Dodonaea* genus. The *Dodonaea* genus comprises about 70 species including, for example, *Dodonaea adenophora, Dodonaea amblyophylla, Dodonaea angustifolia, Dodonaea angustissima, Dodonaea aptera, Dodonaea attenuate, Dodonaea baueri, Dodonaea biloba, Dodonaea boroniifolia, Dodonaea bursariifolia, Dodonaea caespitose, Dodonaea camfieldii, Dodonaea ceratocarpa, Dodonaea concinna, Dodonaea coriacea, Dodonaea cuneata, Dodonaea divaricate, Dodonaea ericifolia, Dodonaea ericoides, Dodonaea falcate, Dodonaea filifolia, Dodonaea filiformis, Dodonaea glandulosa, Dodonaea hackettiana, Dodonaea heteromorpha, Dodonaea hexandra, Dodonaea hirsute, Dodonaea humifusa, Dodonaea humilis, Dodonaea inaequifolia, Dodonaea intricate, Dodonaea lanceolata, Dodonaea larreoides, Dodonaea lobulate, Dodonaea macrossanii, Dodonaea madagascariensis, Dodonaea megazyga, Dodonaea microzyga, Dodonaea multijuga, Dodonaea oxyptera, Dodonaea pachyneura, Dodonaea peduncularis, Dodonaea petiolaris, Dodonaea physocarpa, Dodonaea pinifolia, Dodonaea pinnata, Dodonaea platyptera. Dodonaea polyandra, Dodonaea polyzyga, Dodonaea procumbens, Dodonaea ptarmicifolia, Dodonaea rhombifolia, Dodonaea rigida, Dodonaea rupicola, Dodonaea serratifolia, Dodonaea sinuolata, Dodonaea spatulate, Dodonaea stenophylla, Dodonaea stenozyga, Dodonaea subglandulifera, Dodonaea tenuifolia, Dodonaea tepperi, Dodonaea triangularis, Dodonaea trifida, Dodonaea triquetra, Dodonaea truncatiales. Dodonaea uncinate, Dodonaea vestita*, and *Dodonaea viscose*.

In some embodiments, the plant is of the species *Dodonaea polyandra*.

The compounds may be isolated from the natural source by methods generally known in the art including, for example, chromatography, solvent extraction, and combinations thereof. Column chromatography, thin-layer chromatography, and high-pressure liquid chromatography may be used alone or in combination to isolate the compounds of the invention. Normal phase chromatography, reverse phase chromatography, and combinations thereof, may be used.

The compound may be isolated from an extract of the natural source. Isolating a compound from a natural source may include preparing an extract from the natural source. For example, an extract may be prepared from a suitable plant by i) mixing biomass of the plant with a solvent under appropriate conditions; ii) collecting the solvent containing an extract from step (i); and iii) removing at least a portion of the solvent.

The biomass of the plant may be provided by different parts of the plant and may comprise fresh or dried plant material. In some embodiments, the biomass comprises dried plant material.

In some embodiments, the biomass may comprise any one or more of leaves, stems, or bark. In some embodiments, the biomass may comprise flowers, roots, branches or a trunk.

In some embodiments, the biomass may be crushed, torn, broken, macerated, blended or shredded prior to or concurrent with mixing with the solvent. Alternatively, the biomass may be used in a substantially undamaged state.

As set out above, preparing an extract from a plant includes mixing biomass of the plant with a solvent under appropriate conditions. As will be appreciated by those skilled in the art, the appropriate conditions may vary depending on the solvent used and the components of the plant that are to be extracted.

In some embodiments, the appropriate conditions comprise a temperature between 20° C. and 30° C. In some embodiments, the appropriate conditions comprise a temperature between 20° C. and 40° C.

In some embodiments, the appropriate conditions comprise agitation of the plant material and solvent.

Agitation may be performed by a number of different methods including, for example, stirring, shaking, inversion, etc. In some embodiments, the agitation may be sufficient to rupture or damage the plant biomass, which may be advantageous for the extraction of some compounds from the plant biomass.

Any suitable extraction time may be used to prepare the extract. In some embodiments, mixing biomass of the plant with a solvent under appropriate conditions may be performed for longer than approximately 1, 4, 6, 8, 10, 12, 16, 20 or 24 hours. In some embodiments, mixing biomass of the plant with a solvent under appropriate conditions may be performed for less than 1 hour.

In some embodiments, collecting the solvent containing the extract from the mixture of the biomass of the plant and the solvent involves separating the solvent containing the extract from the biomass of the plant (e.g. by filtration). In some embodiments, the extract may be contained in only a portion or a component of the solvent (e.g. in an aqueous phase or organic phase), in which case collecting the solvent containing the extract may comprise separating one or more portions or components of the solvent. Collection or separation methods include those known in the art including, for example, decanting, filtering, density gradient separation, centrifugation, etc.

The method for preparing the extract also includes removing at least a portion of the solvent. While removing at least a portion of the solvent may be performed prior to the collection of the solvent containing the extract, it is envisaged that this step will normally be performed after collection of the solvent containing the extract. In some embodiments, removing at least a portion of the solvent may comprise removing a component of the solvent (e.g. removal of ethanol from an aqueous ethanol solvent) or may comprise removing at least a portion or volume of the solvent as a whole (e.g. removing 40% of the volume of the solvent). In some embodiments, only a portion of the solvent may be removed thereby concentrating the extract in the remaining solvent or changing the concentration of components in the solvent. In some embodiments, substantially all the solvent may be removed to prepare a dry or solid extract, or all of one or more components of the solvent may be removed.

Methods for removing solvents or components of solvents are known in the art and include, for example, precipitation of the extract, evaporation of the solvent or components of the solvent, chromatography, density gradient separation and/or centrifugation. Evaporation may be promoted by increasing/decreasing the temperature and/or pressure (e.g. freeze drying, baking, rotary evaporation, etc). Which components of a solvent and how much of the solvent is removed may depend on the desired form and use of the extract and the particular solvent that is used.

In some embodiments, the solvent comprises an alcohol. As will be appreciated, a range of different alcohols may be used including, for example, primary (e.g. ethanol), secondary (e.g. isopropyl alcohol) or tertiary (e.g. tert-butyl alcohol) alcohols. In some embodiments, the alcohol may be mixed with water.

In some embodiments, the solvent comprises ethanol or methanol. The solvent could also be aqueous (e.g. 50-99%) methanol or ethanol.

In some embodiments, the solvent comprises an ester such as ethyl acetate.

In some embodiments, the solvent comprises a hydrocarbon. The hydrocarbon may comprise a linear hydrocarbon, a branched hydrocarbon or a cyclic hydrocarbon. In some embodiments, the hydrocarbon may be a substituted hydrocarbon.

In some embodiments, the solvent comprises an alkane hydrocarbon. The alkane hydrocarbon may comprise, for example, a pentane, a hexane or an octane hydrocarbon.

In some embodiments, the alkane hydrocarbon comprises hexane.

In some embodiments, the solvent comprises a halogenated hydrocarbon. In some embodiments, the halogenated hydrocarbon is methylene chloride (i.e. dichloromethane). In some embodiments, the methylene chloride may be mixed with other organic compounds. Accordingly, in some embodiments, the solvent may comprise a mixture of methylene chloride and methanol. While different ratios of methylene chloride to methanol may be used depending on the extract to be extracted and the extraction conditions, in some embodiments, the ratio of methylene chloride to methanol is approximately 1:1.

The method for preparing an extract may comprise a single extraction step with a single solvent or may comprise two or more sequential extraction steps with two or more different solvents or solvents of different concentrations. Thus, in some embodiments, the method comprises a sequential extraction with different solvents. In some embodiments, the method may comprise a single extraction step with multiple solvent.

The term "sequential extraction" as used herein is meant that the biomass is mixed with a first solvent under appropriate conditions and for an appropriate duration before the first solvent is removed and replaced with a second solvent. Further solvents may then be used once the second solvent has been removed. The different solvents may be used in a specific order to remove different components from the plant biomass, which may allow extracts to be selected which include a first component but which exclude a second component. For example, a first solvent, which is suitable for extracting a first component but not a second component from a plant biomass, may be used on the plant biomass prior to a second solvent which would otherwise extract both components. As the first solvent has already extracted the first component from the plant biomass, the second solvent will be able to extract the second component from the plant biomass with minimal amounts of the first component being extracted.

It will be appreciated that a range of different solvents may be used for the sequential extraction including, for example, any of the solvents previously mentioned herein. In some embodiments, the different solvents comprise hexane, methylene chloride/methanol (1:1), and ethanol. In some embodiments, the different solvents may be used in any order. In some embodiments, the different solvents are used in the order hexane then methylene chloride/methanol (1:1), and then ethanol. In some embodiments, the solvents may be pooled at the end of extraction.

In some embodiments, the solvent extraction of the biomass of the plant may be repeated. The solvent containing the extract collected from the repeated solvent extraction may be combined with the solvent containing the extract collected from the original solvent extraction, or it may be processed separately.

Exemplary examples of "extracts" include the "LH" fractions (e.g. LH1-LH13) and the "DPS" fractions referred to in the examples herein.

While in some embodiments, the compound may be directly isolated from a natural source, it is envisaged that an intermediary step (e.g. preparation of an extract) will generally be used. In some embodiments, isolating the compound from an extract instead of directly from the natural source may improve the yield, purity or quality of the compound isolated or improve the efficacy of the isolation process.

In some embodiments, the extract is subjected to chromatography in order to isolate, in a pure form, the compounds of the invention. Suitable chromatography techniques include (but are not limited to): gravity fed column chromatography; medium pressure column chromatography; high pressure column chromatography (e.g. 'flash' chromatography, HPLC, etc); thin layer chromatography; etc. The chromatography may be carried out on normal phase silica, reverse phase silica (e.g. C18), sephadex, etc.

Alternatively, or in addition, the compounds may be obtained by crystallisation using suitable solvent(s).

Suitable solvents include a mixture of a first solvent, in which the compound is soluble, and a second solvent, in which the compound is insoluble. The skilled person will appreciate that an appropriate solvent or combination of solvents can be determined by trial and error.

Exemplary compounds that may be isolated from extracts include the compounds referred to in the examples herein (e.g. compounds C, E, F and H).

Activity-guided fractionation may be utilised in the isolation of compounds from a natural source. In various embodiments, the activity of extracts may be assayed in a suitable inflammation model system and the results of the assay used to identify extracts having suitable anti-inflammatory activity. In some embodiments, the inflammation model system is the mouse ear oedema model.

A second aspect of the invention provides a composition comprising the compound of the first aspect of the invention. The composition may be a pharmaceutical composition or a cosmetic composition.

In some embodiments, of the second aspect of the invention the composition is a pharmaceutical composition comprising a pharmaceutically acceptable carrier. In specific embodiments, the pharmaceutical composition comprises a topical composition.

The pharmaceutical composition may also include one or more pharmaceutically acceptable additives, including pharmaceutically acceptable salts, amino acids, polypeptides, polymers, solvents, buffers, excipients and bulking agents, taking into consideration the particular physical and chemical characteristics of the compound to be administered.

The preparation of such pharmaceutical compositions is known in the art, for example as described in Remington's Pharmaceutical Sciences (18th ed., Mack Publishing Co., Easton, Pa., 1990) and U.S. Pharmacopeia: National Formulary (Mack Publishing Company, Easton, Pa., 1984).

For example, the compound may be prepared into a variety of pharmaceutical compositions in the form of, e.g., an aqueous solution, an oily preparation, a fatty emulsion, an emulsion, a gel, etc., and these preparations may be administered as intramuscular or subcutaneous injection or as injection to an organ, or as an embedded preparation or as a transmucosal preparation through nasal cavity, rectum, uterus, vagina, lung, etc. The composition may be administered in the form of oral preparations (for example solid preparations such as tablets, capsules, granules or powders; liquid preparations such as syrup, emulsions or suspensions). Compositions containing the compound may also contain a preservative, stabiliser, dispersing agent, pH controller or isotonic agent. Examples of suitable preservatives are glycerin, propylene glycol, phenol or benzyl alcohol. Examples of suitable stabilisers are dextran, gelatin, a-tocopherol acetate or alpha-thioglycerin. Examples of suitable dispersing agents include polyoxyethylene (20), sorbitan mono-oleate (Tween 80), sorbitan sesquioleate (Span 30), polyoxyethylene (160) polyoxypropylene (30) glycol (Pluronic F68) or polyoxyethylene hydrogenated castor oil 60. Examples of suitable pH controllers include hydrochloric acid, sodium hydroxide and the like. Examples of suitable isotonic agents are glucose, D-sorbitol or D-mannitol.

The composition may also contain other constituents or additives such as a pharmaceutically acceptable carrier, diluent, excipient, suspending agent, lubricating agent, adjuvant, vehicle, delivery system, emulsifier, disintegrant, absorbent, preservative, surfactant, colorant, flavorant or sweetener, taking into account the physical and chemical properties of the compound being administered.

The composition may be administered orally, parenterally, by inhalation spray, adsorption, absorption, topically, rectally, nasally, bucally, vaginally, ocularly, intraventricularly, via an implanted reservoir in dosage formulations containing conventional non-toxic pharmaceutically-acceptable carriers, or by any other convenient dosage form. The term parenteral as used herein includes subcutaneous, intravenous, intramuscular, intraperitoneal, intrathecal, intraventricular, intrasternal, and intracranial injection or infusion techniques.

When administered parenterally, the composition may be in a unit dosage, sterile injectable form (solution, suspension or emulsion) which is preferably isotonic with the blood of the recipient with a pharmaceutically acceptable carrier. Examples of such sterile injectable forms are sterile injectable aqueous or oleaginous suspensions. These suspensions may be formulated according to techniques known in the art using suitable dispersing or wetting agents and suspending agents. The sterile injectable forms may also be sterile injectable solutions or suspensions in non-toxic parenterally-acceptable diluents or solvents, for example, as solutions in 1,3-butanediol. Among the acceptable vehicles and solvents that may be employed are water, saline, Ringer's solution, dextrose solution, isotonic sodium chloride solution, and Hanks' solution. In addition, sterile, fixed oils are conventionally employed as solvents or suspending media. For this purpose, any fixed oil may be employed including synthetic mono- or di-glycerides, corn, cottonseed, peanut, and sesame oil. Fatty acids such as ethyl oleate, isopropyl myristate, and oleic acid and its glyceride derivatives, including olive oil and castor oil, especially in their polyoxyethylated versions, are useful in the preparation of injectables. These oil solutions or suspensions may also contain long-chain alcohol diluents or dispersants.

The carrier may contain minor amounts of additives, such as substances that enhance solubility, isotonicity, and chemical stability, for example anti-oxidants, buffers and preservatives.

When administered orally, the compound may be formulated into unit dosage forms such as tablets, cachets, powder, granules, beads, chewable lozenges, capsules, liquids, aqueous suspensions or solutions, or similar dosage forms, using conventional equipment and techniques known in the art. Such formulations typically include a solid, semisolid, or liquid carrier. Exemplary carriers include lactose, dextrose, sucrose, sorbitol, mannitol, starches, gum acacia, calcium phosphate, mineral oil, cocoa butter, oil of theobroma, alginates, tragacanth, gelatin, syrup, methyl cellulose, polyoxyethylene sorbitan monolaurate, methyl hydroxybenzoate, propyl hydroxybenzoate, talc, magnesium stearate, and the like.

A tablet may be made by compressing or moulding the compound optionally with one or more accessory ingredients. Compressed tablets may be prepared by compressing, in a suitable machine, the active ingredient in a free-flowing form such as a powder or granules, optionally mixed with a binder, lubricant, inert diluent, surface active, or dispersing agent. Moulded tablets may be made by moulding in a suitable machine, a mixture of the powdered active ingredient and a suitable carrier moistened with an inert liquid diluent.

The administration of the compound in the various embodiments of the present invention may also utilise controlled release technology. The compound may also be administered as a sustained-release pharmaceutical. To further increase the sustained release effect, the compound may be formulated with additional components such as vegetable oil (for example soybean oil, sesame oil, camellia oil, castor oil, peanut oil, rape seed oil); middle fatty acid triglycerides; fatty acid esters such as ethyl oleate; polysiloxane derivatives; alternatively, water-soluble high molecular weight compounds such as hyaluronic acid or salts thereof (weight average molecular weight: ca. 80,000 to 2,000,000), carboxymethylcellulose sodium (weight average molecular weight: ca. 20,000 to 400,000), hydroxypropylcellulose (viscosity in 2% aqueous solution: 3 to 4,000 cps), atherocollagen (weight average molecular weight: ca. 300,000), polyethylene glycol (weight average molecular weight: ca. 400 to 20,000), polyethylene oxide (weight average molecular weight: ca. 100,000 to 9,000,000), hydroxypropylmethylcellulose (viscosity in 1% aqueous solution: 4 to 100,000 cSt), methylcellulose (viscosity in 2% aqueous solution: 15 to 8,000 cSt), polyvinyl alcohol (viscosity: 2 to 100 cSt), polyvinylpyrrolidone (weight average molecular weight: 25,000 to 1,200,000).

In some embodiments, the compound may be incorporated into a hydrophobic polymer matrix for controlled release over a period of days. The compound may then be moulded into a solid implant, or externally applied patch, suitable for providing efficacious concentrations of the compound over a prolonged period of time without the need for frequent re-dosing. Such controlled release films are well known to the art. Other examples of polymers commonly employed for this purpose that may be used include nondegradable ethylene-vinyl acetate copolymer a degradable lactic acid-glycolic acid copolymers which may be used externally or internally. Certain hydrogels such as poly(hydroxyethylmethacrylate) or poly(vinylalcohol) also may be useful, but for shorter release cycles than the other polymer release systems, such as those mentioned above.

The carrier may also be a solid biodegradable polymer or mixture of biodegradable polymers with appropriate time release characteristics and release kinetics. The compound may then be moulded into a solid implant suitable for providing efficacious concentrations of the compound over a prolonged period of time without the need for frequent re-dosing. The compound can be incorporated into the biodegradable polymer or polymer mixture in any suitable manner known to one of ordinary skill in the art and may form a homogeneous matrix with the biodegradable polymer, or may be encapsulated in some way within the polymer, or may be moulded into a solid implant.

In some embodiments, the composition may be a topical composition. For topical administration, the composition of the present invention may be in the form of a solution, spray, lotion, cream (for example a non-ionic cream), gel, paste, ointment or lozenge. Alternatively, the composition may be delivered via a liposome, nanosome, or nutri-diffuser vehicle.

In some embodiments, the topical composition is adapted for administration to skin or gums. For example the composition may be provided in the form of a cream, a lotion, a paste, an ointment, a gel, etc.

Creams may be formulations that contains water and oil and is stabilised with an emulsifier. Lipophilic creams are called water-in-oil emulsions, and hydrophilic creams oil-in-water emulsions. The cream base for water-in-oil emulsions may be absorption bases such as vaseline, ceresin or lanolin. The bases for oil-in-water emulsions may be mono-, di- and triglycerides of fatty acids or fatty alcohols with soaps, alkyl sulphates or alkyl polyglycol ethers as emulsifiers.

Lotions may be opaque, thin, non-greasy emulsion liquid dosage forms for external application to the skin, which may contain a water-based vehicle with greater than 50% of volatiles and sufficiently low viscosity that it may be delivered by pouring. Lotions are usually hydrophilic, and contain greater than 50% of volatiles as measured by LOD (loss on drying). A lotion tends to evaporate rapidly with a cooling sensation when rubbed onto the skin.

Pastes may be opaque or translucent, viscous, greasy emulsion or suspension semisolid dosage forms for external application to the skin, which may contain greater than 50% of hydrocarbon-based or a polyethylene glycol-based vehicle and less than 20% of volatiles. A paste may contain a large proportion (20-50%) of dispersed solids in a fatty or aqueous vehicle. An ointment tends not to evaporate or be absorbed when rubbed onto the skin.

Ointments may be opaque or translucent, viscous, greasy emulsion or suspension semisolid dosage forms for external application to the skin, which may contain greater than 50% of hydrocarbon-based or a polyethylene glycol-based vehicle and less than 20% of volatiles. An ointment is usually lipophilic, and contains >50% of hydrocarbons or polyethylene glycols as the vehicle and <20% of volatiles as measured by LOD. An ointment tends not to evaporate or be absorbed when rubbed onto the skin.

Gels may be translucent, non-greasy emulsion or suspension semisolid dosage forms for external application to the skin, which contains a gelling agent in quantities sufficient to impart a three-dimensional, cross-linked matrix. A gel is usually hydrophilic, and contains sufficient quantities of a gelling agent such as starch, cellulose derivatives, carbomers, magnesium-aluminum silicates, xanthan gum, colloidal silica, aluminium or zinc soaps.

Compositions for topical administration may further include drying agents, anti-foaming agents; buffers, neutralising agents, agents to adjust pH; colouring agents and decolouring agents; emollients; emulsifying agents, emulsion stabilisers and viscosity builders; humectants; odorants; preservatives, antioxidants, and chemical stabilisers; solvents; and thickening, stiffening, and suspending agents, and a balance of water or solvent. In some embodiments, the topical formulation may also be in the form of a spray. Examples of suitable spray formulations include nasal sprays, mouth or throat sprays and skin sprays.

In some embodiments, the composition may be an ocular composition. For ocular administration, the composition of the present invention may be in the form of a solution, spray, lotion, cream, gel, paste or ointment.

Drops and solutions applied directly to the eye are typically sterilised aqueous solutions containing 0.1% to 10%, along with suitable buffer, stabiliser, and preservative. The total concentration of solutes should be such that, if possible, the resulting solution is isotonic with the lacrimal fluid and has an equivalent pH in the range of pH 6-8. Typical preservatives are phenyl mercuric acetate, thimerosal, chlorobutanol, and benzalkonium chloride. Typical buffer systems and salts are based on, for example, citrate, borate or phosphate; suitable stabilisers include glycerin and polysorbate 80. The aqueous solutions are formulated simply by dissolving the solutes in a suitable quantity of water, adjusting the pH to about 6.8-8.0, making a final volume adjustment with additional water, and sterilising the preparation using methods known to the person skilled in the art.

The dosage level of the resulting ocular composition will, of course, depend on the concentration of the drops, the condition of the subject and the individual magnitude of responses to treatment. However, a typical ocular composition could be administered at the rate of about 2-10 drops per day per eye of a 0.5% solution of active ingredient.

The pharmaceutical composition may be used in conventional medicinal regimes, complementary medicine regimes, and/or alternative medicine regimes.

In some embodiments of the second aspect of the invention, the composition is a cosmetic composition. Cosmetic compositions may be prepared by mixing any one or more of the compounds of the first aspect of the invention with cosmetically acceptable carriers, diluents and/or adjuvants. In these embodiments, the compounds may be incorporated into topical vehicles, such as cosmetic vehicles, for application to the skin of a subject. Suitable cosmetic vehicles include, but are not limited to: make up, products intended for application to the lips, face masks and scrubs, cleansing products such as lotions, skin softeners, powders, conditioning products such as lotions, creams, oils, anti-ageing products, skin whitening products, hairdressing products such as lotions and lacquers, deodorants, antiperspirants, cleansers such as toilet soap, deodorant soap, astringent and skin washes, shaving products such as creams, foams and lotions, bath and shower preparations such as salts, foams, oils, gels, etc., depilatories, after-bath powders, hygienic powders, moisturising products such as creams, lotions, gels and foams, sunbathing products. The cosmetic product may be a leave-on composition, a rinsing composition or a cleansing composition.

In one embodiment, the cosmetic product may be selected from the group consisting of: an essence, a cleanser, a toner, a cream, a mask, and a mist.

The compositions may further comprise additional antioxidants, sun-blocking agents, moisturisers, essential oils, plant extracts, skin conditioning agents, herbal extracts, humectants, surfactants, vitamins, thickening agents, preservatives, exfoliants, fragrances, and the like.

Exemplary antioxidants include water-soluble antioxidants such as sulfhydryl compounds and their derivatives (for example sodium metabisulfite and N-acetyl-cysteine), lipoic acid and dihydrolipoic acid, resveratrol, and lactoferrin. Exemplary oil-soluble antioxidants include butylated hydroxytoluene, retinoids, tocopherols, and ubiquinone.

Exemplary moisturisers include fatty acids, lanolin, cetyl palmitate, castor oil, jojoba seed oil, grape seed oil, sunflower seed oil, safflower seed oil, diglycerin, oleic acid, dimethicone copolyol, dextrin, jojoba esters, panthenol, squalene, coconut oil, olive oil, gelatin, cocoa butter, hydrogenated lecithin, isopropyl isostearate, hydrogenated vegetable oil, glycerol polymers, glycerin, sorbitan palmitate, petrolatum, tri-stearin, glyceryl distearate, and ceramides.

Essential oils may enhance the emollient and penetration properties of the composition. Exemplary essential oils include lemongrass oil, tea tree oil, thyme oil, lavender oil and alpha Bisabolol.

Exemplary humectants include glycerol, sorbitol, polyethylene glycol, and mono- and oligomeric sugars.

Exemplary vitamins include vitamin A, pro vitamin A, vitamin Bi, vitamin $B_2$, vitamin $B_3$, vitamin $B_4$, vitamin $B_5$, vitamin $B_6$, vitamin $Bi_2$, vitamin D, vitamin $D_2$, vitamin $D_3$, tocopherol (vitamin E), vitamin F, and vitamin Ki.

Exemplary thickening agents include carbomers, hydroxymethyl cellulose, xanthan gum, guar gum, chitosan, stearyl alcohol, and polyquaternium-10.

Exemplary preservatives include totarol, parabens, quaternary ammonium chlorides, benzalkonium chlorides, isothiazolinones, parabens, chloroxylenol; chlorhexidine, phenoxyethanol, benzyl alcohol, phenethyl alcohol, benzoic acid and salts thereof, chlorobutanol, sorbic acid and salts thereof, triclosan, and triclocarban.

Exemplary skin conditioning agents include hydroxyacids. The term "hydroxyacids" includes both α- and β-hydroxyacids. Suitable hydroxyacids include, but are not limited to α-hydroxyacids such as lactic acid, glycolic acid, citric acid, α-hydroxyoctanoic acid, tartaric acid, glucoronic acid, α-hydroxybutyric acid, malic acid, mandelic acid, and pyruvic acid. Suitable β-hydroxy acids include but are not limited to salicylic acid, β-hydroxy butyric acid, and carnitine.

The cosmetic composition may be used to treat or prevent inflammation in a subject.

A third aspect of the invention provides a method of treating or preventing inflammation in a subject, the method comprising administering to the subject a therapeutically effective amount of the compound according to the first aspect of the invention.

A fourth aspect of the invention provides a method of treating or preventing inflammation in a subject, the method comprising administering to the subject a therapeutically effective amount of a composition of the second aspect of the invention.

In some embodiments, the inflammation comprises acute inflammation. In some embodiments, the acute inflammation in the subject may be in response to any one or more of the following: a wound (e.g. a cut, bruise, burn, etc); an infection (e.g. bacterial, viral, fungal, protist, etc); exposure to a toxin or ionising radiation; exposure to an allergen or antigen; and the presence of a foreign body (e.g. a splinter) in the subject. In some embodiments, the acute inflammation may be associated with dermatitis.

In some embodiments, the inflammation comprises chronic inflammation. In some embodiments, the chronic inflammation may be associated with a persistent form of an acute inflammation, as described above, or may be associated with an inflammatory disorder. Inflammatory disorders may comprise, for example, an autoimmune disease (e.g. rheumatoid arthritis, Crohn's disease, inflammatory bowel disease, sarcoidosis, psoriasis, multiple sclerosis, etc), a hypersensitivity reaction against innocuous environmental antigens (e.g. asthma, eczema, hay fever, urticaria, food allergy, etc), a hypersensitivity reaction against a persistent infection or a delayed hypersensitivity reaction such as contact hypersensitivity, tuberculin-type hypersensitivity or granulomatous hypersensitivity.

In some embodiments, the inflammation may be associated with other diseases or conditions, including, for example, glomerulonephritis, spondylitis, osteoarthritis, vasculitis, scleroderma, Still's disease, gingivitis, etc.

Accordingly, in some embodiments, the present invention provides a method of treating a disease or condition characterised by or associated with inflammation, the method comprising administering to a subject in need of such treatment a therapeutically effective amount of a compound according to the first aspect of the invention or a therapeutically effective amount of a composition according to the second aspect of the invention.

In some embodiments, the inflammation is associated with an immune response to a transplanted organ or tissue.

The symptoms of the inflammation will depend on the type of inflammation but may include any one or more of the following: redness; increased heat; swelling; pain; and loss of function of the affected tissue.

In some embodiments, the inflammation may be mediated by any one or more of the following immune reactions or processes: T cell activation; B cell activation; dendritic cell activation; activation of the innate immune cells (i.e. phagocytic cells including, for example, monocytes, macrophages, neutrophils, etc.); release of chemotactic molecules; release of complement; release of pro-inflammatory cytokines; abrogation of anti-inflammatory cytokines; release of antibodies; migration of immune cells to a site of injury, infection, etc.; increased blood supply to a site of injury, infection, etc.; an increase in vascular permeability near a site of injury, infection, etc; and increased expression of adhesion molecules by cells near a site of injury, infection, etc. In some embodiments, the compound or the pharmaceutical composition may inhibit any one or more of these immune reactions or processes.

Administering the compound or the composition to the subject may comprise administration by any suitable method. For example, the compound or the pharmaceutical composition may be administered orally, parenterally, topically, endoscopically, by injection, systemically or by any other suitable means.

As set out above, the method according to the third or fourth aspect of the present invention may be used to treat or prevent inflammation in a subject. In some embodiments, the subject is an animal subject. Suitable subjects include, for example, mammalian subjects such as humans, primates, livestock animals such as horses, cattle, sheep, pigs, goats or the like, companion animals such as dogs or cats, laboratory test animals such as mice, rats, guinea pigs or birds, or animals of veterinary significance, or animals of economic significance. The subject may also include non-mammalian animal subjects such as birds including poultry birds such as chickens; reptilian subjects including companion reptiles such as turtles, tortoises and snakes; fish including wild-caught fish and fish in aquaculture.

Accordingly, in some embodiments, the subject is a mammal. In some embodiments, the subject is a human.

A fifth aspect of the invention provides use of the compound of the first aspect of the invention, in the preparation of a medicament for the treatment or prevention of inflammation.

A sixth aspect of the invention provides use of the compound of the first aspect of the invention, in the treatment of a disease or condition characterised by or associated with inflammation.

The present invention is further described by the following non-limiting figures and/or examples.

BRIEF DESCRIPTION OF THE FIGURES

FIG. 1 shows a table of the anti-inflammatory activities and % yields of different crude extracts obtained from leaves of Dodonaea polyandra.

FIG. 5 shows a table of the anti-inflammatory activities and % yields of crude extracts obtained from stems of Dodonaea polyandra at 0.4 mg, 0.04 mg and 0.004 mg per ear with croton oil was used as a positive control for inflammation.

FIG. 13 shows the percentage maximum and average inhibition of inflammation in a murine model of inflammation using semi-pure fractions of hexane leaf extracts from Dodonaea polyandra. The semi-pure fractions 1-13 are as provided in FIG. 6.

EXAMPLES

Example 1

Figure 2:
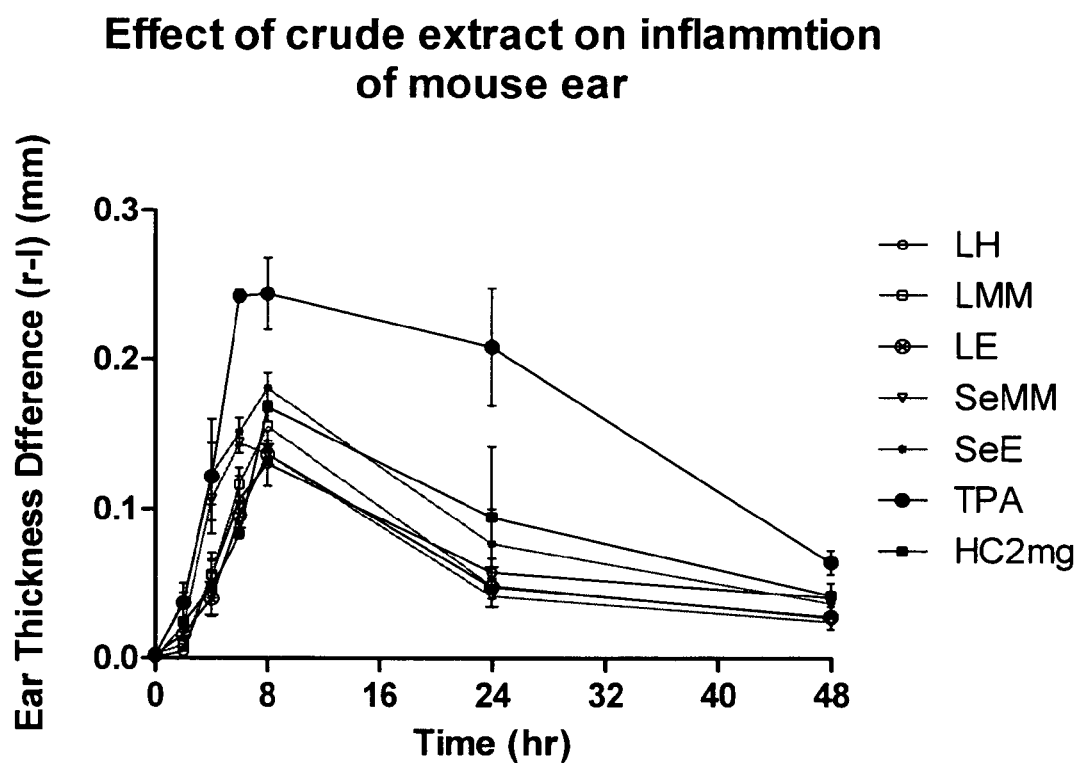
FIG. 2 shows a graph of the anti-inflammatory effects of the crude extracts obtained from leaves of Dodonaea polyandra (at 0.4 mg/ear) in a murine ear model of inflammation (LH=n-hexane extracted, LMM=methylene chloride/methanol (1:1) extracted, LE=80% ethanol extracted, SeMM=sequential methylene chloride/methanol extracted, SeE=sequential 80% ethanol extracted, TPA=12-O-tetradecanoylphorbol 13-acetate).

Collection of Plant Material from Dodonaea polyandra

Plant material from Dodonaea polyandra was collected by Northern Kaanju people on Northern Kaanju Kuku I'yu Homelands (at Chuula Homelands), Central Cape York Peninsula, Queensland in collaboration with ethnobotanist Mr Nick Smith who confirmed the Western scientific species names. The leaves and stems of Dodonaea polyandra (voucher number NMS5293) were collected from a population of 30 plant samples from both male and female types (juveniles ≤2 µm) in December 2007. Voucher specimens and details of plant location (13°07'14", 142°59'45") were recorded and lodged at Brisbane Herbarium, Queensland (voucher specimen number AQ 749703). Plant material was allowed to air dry in the shade and packed into paper bags for transportation. Leaves and stems were then separated from one another and stored in separate paper bags at −20° C. until extraction.

Example 2

General Materials

All solvents used for plant extraction and crude separations were analytical grade (Merck, Australia and Univar, Australia) or HPLC grade (Merck, Australia and Univar, Australia) for HPLC experiments. Thin-layer chromatography (TLC) plates (reverse phase RP-18 F254 and normal phase Silica gel 60 $F_{254}$) were purchased from Merck (Darmstadt, Germany). Plates were visualised under UV light (254/365 nm) using a Chromato-vue cabinet CC-60 (UVP, Australia). Waters C18 125 Å (Milford, Mass.), Merck Silica gel 60 (70-230 mesh ASTM) and Sephadex LH-20 (Sigma) were used for column chromatography. All HPLC experiments were carried out on a Shimadzu SIL-10 Å with auto injector, SCL-10A system with Activon GoldPak 100 5 μm ODS 25×1 cm or Activon GoldPak Silica Gel 5 μm semi-preparative HPLC columns. Optical rotations were conducted using a PolAAr 21 polarimeter (589 nm, 20° C.). 1D and 2D NMR data were acquired on a Varian INOVA 600 MHz spectrometer ($CDCl_3$ or $CD_3OD$) at the University of Adelaide. HREIMS and/or HRAPCI mass spectra were obtained on a Kratos Concept ISQ magnetic sector or ThermoFinnegan LTQ Orbitrap HR MS/MS at the Central Science Laboratory, University of Tasmania. Infrared and UV spectroscopy was carried out using a Shimadzu 8400S FT-IR (Shimadzu, Japan) and CARY 50 Bio (Varian, USA), respectively.

Example 3

Aqueous Alcoholic Solvent Extraction of Leaf and Stem Material

Leaf plant material (50 g) and stem plant material (50 g) from example 1 were separately extracted with 80% (v/v) aqueous ethanol using a solvent to dry plant material ratio of 5:1 at 25° C. with agitation for 24±1 h. After 24 h the ethanolic extract was decanted and filtered in vacuo through Whatman No. 1 filter paper (Whatman, UK). A second equivalent amount of solvent was added and allowed to extract for a further 24 hrs before removal and filtration. The filtered extract was concentrated using Buchi Rotavap at 40-42° C. to remove ethanol and subsequently freeze-dried (Christ Alpha 2-4 LD) to remove residual water. The yield for the leaf extract (LE) and stem extract (SE) was 34.4% (17.7 g) and 14.0% (7.02 g), respectively. Long-term storage of dried extract was at −20° C.

Example 4

Non-Sequential and Sequential Extraction of Leaf and Stem Material Using Different Organic Solvents Extracts of the leaf material and stem material from example 1 were individually prepared using the method described in example 3 but using n-hexane and methylene chloride/methanol (1:1) as the solvents. In addition, a batch of leaf material and a batch of stem material were extracted sequentially starting with n-hexane then methylene chloride/methanol (1:1) and lastly 80% (v/v) aqueous ethanol with plant material being extracted once only with the respective solvents. The leaf yields for n-hexane (LH) and methylene chloride/methanol (1:1) (LMM) extracts were 1.2% (600 mg) and 22.3% (11.1 g), respectively. Meanwhile, for the sequential method the leaf yields were 1.34% (670 mg), 15.4% (7.69 g) and 14.1% (7.03 g) for the n-hexane (SeLH), methylene chloride/methanol (1:1) (SeLMM) and 80% (v/v) aqueous ethanol (SeLE) extracts, respectively. Long-term storage of dried extracts was at −20° C.

Example 5

Mouse Ear Oedema Model

Anti-inflammatory activity was measured in the mouse ear oedema model using 12-O-tetradeconoylphorbol-13-acetate (TPA) (Sigma) or croton oil as the inducer of inflammation (Sanchez, T and Moreno, J 1999, Role of leukocyte influx in tissue prostaglandin H synthase-2 overexpression induced by phorbol ester and arachidonic acid in skin, Biochemical Pharmacology, 58, 877-879.). Male Balb/C mice 7-9 weeks old and weighing 20-25 g were used. Mice were housed in cages at constant room temperature (20±2° C.) with access to food (standard rat/mouse pellet) and water ad libitum. A 12 hr day/night cycle was maintained in the animal holding facility (Reid building animal house, University of South Australia) and all experiments were carried out during the day phase.

Baseline measurements of ear thickness were measured using a digital micrometer (±0.001 mm, Mitutoyo, Japan) prior to the experiment. TPA (2.5 μg/ear), which was dissolved in acetone, was then applied in a volume of 20 μL to the inner surface of the right ear and 20 μL of acetone to the left ear as control. After thirty minutes the test samples, which were dissolved in 80% ethanol, were applied to the inner surface of the right ear and 80% ethanol on the left ear to the respective treatment groups. Betamethasone 17,21-dipropionate (Sigma) (0.9 μmol/ear) was used as a positive control. Multi-dose experiments were conducted over the range 0.005-1.83 μmol/ear. At 2 h, 4 h, 6 h, 8 h, 24 h and 48 h after the application, the ear thicknesses were measured using a digital micrometer. A non-treated control group to which only croton oil or TPA were applied was used as a measure of maximum inflammation achieved with percent inhibition of inflammation of test sample being calculated relative to this group. Following completion of the experiment, mice were euthanized by inhalation of isoflurane followed by cervical dislocation.

Example 6

Crude Leaf Extracts of D. Polyandra Inhibit Inflammation in the Mouse Oedema Model The anti-inflammatory properties of the crude extracts prepared in example 3 and example 4 were tested in the TPA-induced mouse ear oedema model of acute inflammation as described in example 5.

Figure 3:
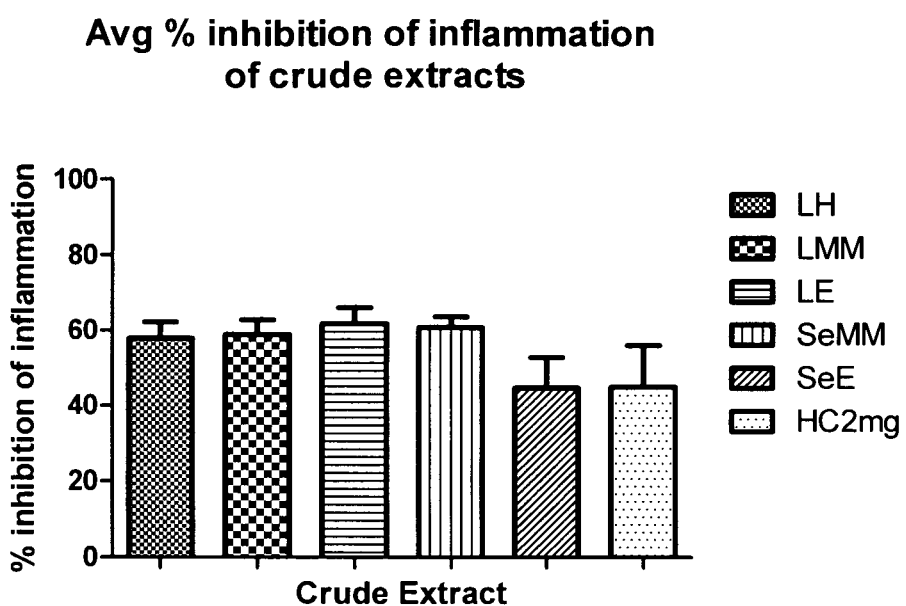
FIG. 3 shows a graph of the average percent inhibition of inflammation due to the crude extracts obtained from leaves of Dodonaea polyandra in a murine ear model of inflammation (LH=n-hexane extracted, LMM=methylene chloride/methanol (1:1) extracted, LE=80% ethanol extracted, SeMM=sequential methylene chloride/methanol extracted, SeE=sequential 80% ethanol extracted, HC=hydrocortisone hemisuccinate salt).

As shown in FIG. 1, each of the crude extracts significantly inhibited inflammation in the mouse oedema model. The levels of inhibition were comparable to or exceeded those of hydrocortisone, which was used as a positive control for inhibition of inflammation. As shown in FIG. 2, the inhibitory effects of the crude extracts followed a similar time course trend as the positive controls. The average inhibition of inflammation by the crude extracts exceeded that of the control or was comparable to the control as indicated in FIG. 3.

Example 7

Stem Extracts of D. Polyandra Inhibit Inflammation in the Mouse Oedema Model The anti-inflammatory properties of the crude stem extracts of D. polyandra were tested in the TPA-induced mouse ear oedema model of acute inflammation as described in example 5.

Figure 4:
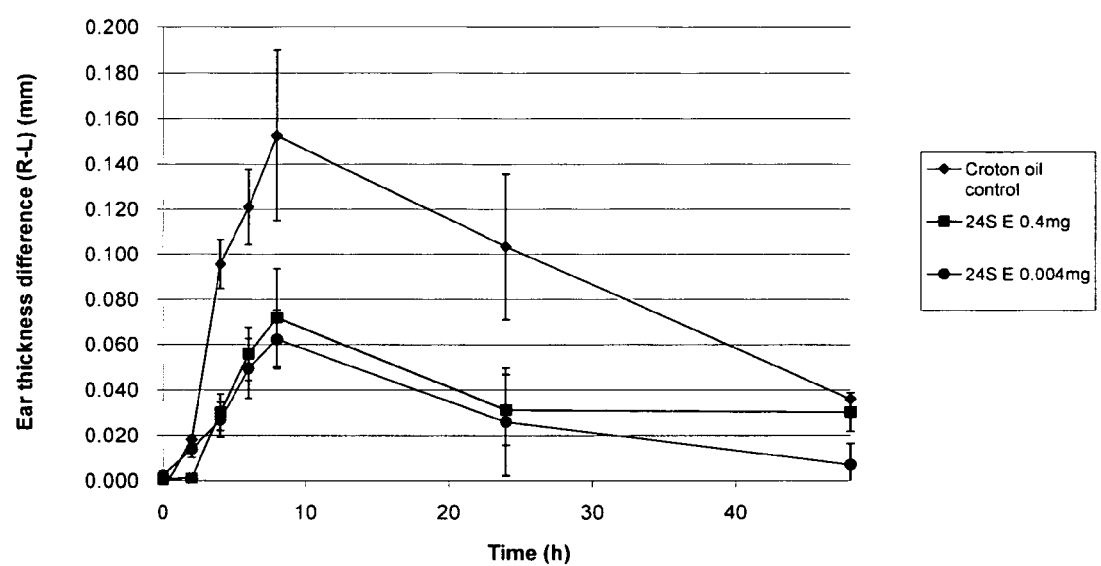
FIG. 4 shows a graph of the ear thickness differences between control ears and ears treated with an extract obtained from stems of Dodonaea polyandra in a murine model of inflammation. The stem extract was administered at 0.4 mg, 0.04 mg and 0.004 mg per ear and croton oil was used as a positive control for inflammation.

As shown in FIG. 4 and FIG. 5, the stem extracts of D. polyandra provided strong inhibition of inflammation at 0.004 mg/ear and 0.4 mg/ear.

Example 8

Fractionation of D. Polyandra Leaf Extract

The crude leaf extract (SeLH) obtained from the n-hexane extraction (example 4) was further fractionated by liquid chromatography.

The initial separation carried out on leaf hexane (SeLH) extract (7 g) was normal phase flash chromatography. The first separation was carried out using a glass column (Ø 45 mm, packing height 120 mm). The crude sample was applied to the column using the pre-adsorption method. The mass ratio of silica gel to crude extract adsorbed was 5:2 (i.e. 2.5 g silica/g sample). The separation was carried out under inert conditions using nitrogen. The eluent used was n-hexane with increasing amounts of $CH_2Cl_2$ up to 100% $CH_2Cl_2$ to which MeOH was introduced beginning with a 99:1 ratio. The separation was ceased once the column had been flushed with $CH_2Cl_2$/MeOH (90:10). Approximately 400 mL of eluent was used for each different composition throughout the separation whilst collecting 20 mL fractions.

Every second fraction was analysed on TLC and pooled into larger fractions based on the observed TLC profile. A total of 13 main fractions were obtained from the initial separation with each subsequently tested in the TPA-induced mouse ear oedema model. A chart showing the fractionation of the LH extract, the yields of the fractions and the level of inhibition of inflammation (I) is provided in FIG. 6. The maximum and percentage inhibition of inflammation of each fraction is also provided in the table of FIG. 12. As shown in the figures, a number of the fractions inhibited inflammation.

A major yellow spot was observed on TLC from fraction (Fr) LH10 which initiated further purification of this fraction. Fraction LH10 (1036 mg) was chromatographed under gravity using lipophilic sephadex LH-20 (Ø 30 mm, packing height 480 mm) with a $CH_2Cl_2$/MeOH (3:1) mobile phase. Five fractions were obtained from this step with Fr-LH10.3 containing the yellow spot of interest. Subsequently the semi-pure Fr-LH10.3 was separated isocratically by reverse phase (C18) HPLC using 80% MeOH/$H_2O$ as eluent and 2 mL/min flowrate. Concentration of the 2 mL fractions and RP-TLC analysis revealed the presence of two yellow spots not previously observed on normal phase TLC. Therefore, the remainder of Fr-LH 10.3.2 was reinjected onto RP-HPLC with the fraction size collected reduced to 1 mL in volume. Reducing the fraction volume resolved the two compounds from one another to afford compounds A (4.8 mg) and B (31 mg) (details not provided) both as yellow gummy solids.

Figure 6:
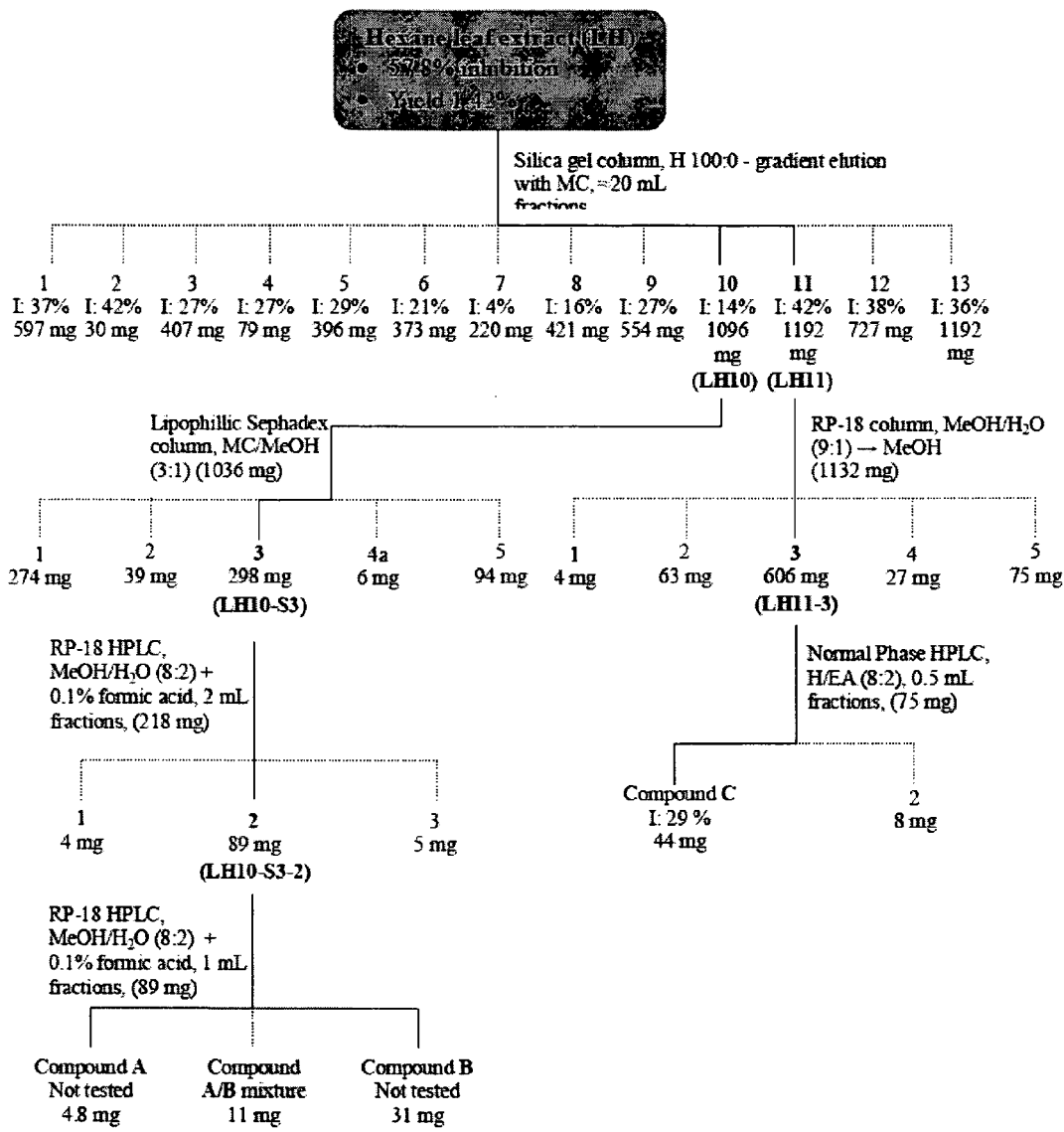
FIG. 6 shows a chart of the fractionation of a hexane leaf extract from Dodonaea polyandra leaves, the yield of the fractions and the inhibitory activity of the fractions. The chart also shows the purification of compounds from the extract, the yield of the compounds and the inhibitory activity of one of the compounds (compound C).
Figure 7:
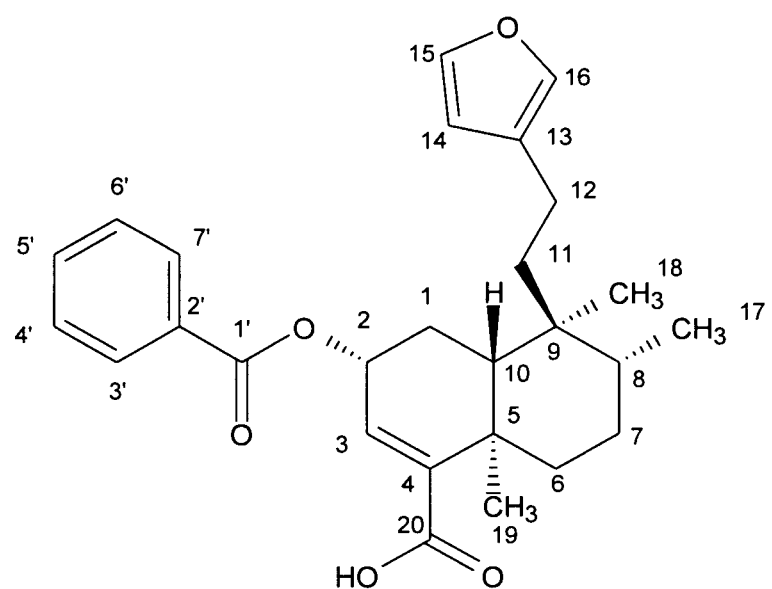
FIG. 7 shows the chemical structure of compound C isolated and tested for inhibitory activity from FIG. 6.

The equally most active fraction LH11 was separated into five subfractions using low-pressure reverse phase (C18) column chromatography. The separation was carried out on a glass column (Ø 30 mm, 150 mm packing height) using isocratic elution with 90% MeOH/$H_2O$. Approximately 5 mL fractions were collected and the separation was continuously monitored by TLC analysis. The spot of interest from this sample was green/blue in appearance upon spraying with anisaldehyde reagent. The remaining components were flushed off with 100% MeOH followed by isopropanol. The bulk of the separation was contained within Fr-LH 11.3 (606 mg) consisting of 3 individual components on the basis of TLC. The components present in Fr-LH 11.3 showed greater resolution on normal phase TLC compared to reverse phase TLC. Therefore, Fr-LH11.3 (75 mg) was further purified using normal phase HPLC with hexane/ethyl acetate (8:2) isocratic elution whilst collecting 0.5 mL fractions. The separation gave 44 mg of compound C (15,16-epoxy-2(α)-benzoyloxy-cleroda-3,13(16),14-trien-18-oic acid; see FIG. 6) as a white amorphous solid. FIG. 6 provides further details of the fractionation and purification of compounds A, B and C. The chemical structure of compound C is shown in FIG. 7. The yield of purified compound C was 44 mg.

Compound C was isolated as a white amorphous solid with the molecular formula $C_{27}H_{32}O_5$ which was determined from the HREIMS molecular ion peak at m/z 436.2245 (calcd for $C_{27}H_{32}O_5$, 436.2250) thus indicating the presence of 12 degrees of unsaturation. The $^1H$ NMR spectrum for compound C (Table 1) showed resonances for aromatic protons ($\delta_H$ 8.01, dd, J=8.4, 1.3 Hz; 7.53, t, J=7.4, 1.3 Hz; 7.37, dd, J=8.4, 7.4 Hz) and the signal at $\delta_H$ 8.01 gave a HMBC correlation to the carbonyl carbon ($\delta_C$ 165.9) of an ester. A vinylic proton at $\delta_H$ 6.77 which initially showed up as a doublet was resolved into a double doublet upon Lorentzian/Gaussian resolution enhancement (dd, J=4.4, 1.4 Hz; $\delta_C$ 132.7) and gave a strong COSY correlation with an oxymethine proton ($\delta_H$ 5.65, dt, J=4.8, 1.4 Hz). In the HMBC spectrum this same proton ($\delta_H$ 5.65) correlated with the ester carbonyl carbon $\delta_C$ 165.9. Given the commonality of a C-3 vinylic proton in clerodane diterpenoids this meant the vinylic proton $\delta_H$ 6.77 was located at C-3 and implied the benzoyl ester functionality was attached at C-2. COSY correlations present between non-identical methylene protons ($\delta_H$ 2.02, dq, J=15.0, 1.8 Hz; 1.95, ddd, J=15.0, 12.8, 5.0 Hz) to $\delta_H$ 5.65 and a methine proton ($\delta_H$ 1.78, dd, J=12.8, 2.0 Hz) and additionally HMBC correlations between $\delta_H$ 1.78 and methyl carbon $\delta_C$ 18.9 ($\delta_H$ 1.29, s) indicated an arrangement of C-2, C-6 and C-10. Resonances for methylene protons attached to $\delta_C$ 35.3 ($\delta_H$ 2.36, m; 1.30, dt, J=12.6, 4.1 Hz) and $\delta_C$ 27.1 ($\delta_H$ 1.51, m; 1.48, m) were assigned to C-6 and C-7, respectively. Furthermore, $\delta_H$ 1.30 showed a HMBC correlation to the methyl group attached to C-5.

Evidence for a third methyl was seen in the DEPT and $^1H$ NMR data. A methyl doublet ($\delta_H$ 0.86, d, J=6.6 Hz) present in the $^1H$ NMR spectrum of compound C coupled with a methine proton ($\delta_H$ 1.64, m) which also showed COSY correlations with the methylene protons $\delta_H$ 1.51, 1.48, thus indicating that the methyl group was positioned at $\delta_C$ 36.1 (C-8). The connectivity for the methyl group ($\delta_H$ 0.79) which appeared as a singlet in the $^1H$ NMR spectrum was determined to be connected at $\delta_C$ 38.5 (C-9) through HMBC correlations with $\delta_C$ 42.1, $\delta_C$ 38.5 and $\delta_C$ 36.1.

Significant peaks in the mass spectrum at m/z 95, 81 and signals for furan protons in the $^1H$ NMR spectrum ($\delta_H$ 7.20, t, J=1.7 Hz; 7.76, dd, J=1.7, 0.9 Hz; 6.00, dd, J=1.7, 0.9 Hz) supported the presence of a β-substituted furanyl group. The connectivity of the ethyl linked β-furan was established to be at $\delta_C$ 38.5 (C-9). Evidence of a carboxylic acid connected at C-4 ($\delta_C$ 146.5) was present. The structural data described above led to this new compound C as 15,16-epoxy-2(α)-benzoyloxy-cleroda-3,13(16),14-trien-18-oic acid.

Similarly as for previously elucidated structures the relative configurations of stereocentres were established using ROESY. The proton at $\delta_H$ 1.78 (C-10) of compound 4 was again assumed to occupy an orientation the same as 1, 2, and 3. The $^{13}C$ resonance of Me-19 and an absence of ROESY correlation between proton $\delta_H$ 1.78 and methyl protons $\delta_H$ 1.29 (Me-19) indicated a trans ring junction. Correlations also existed between all three methyl groups implying their co-facial relationship. The oxymethine proton at C-2 gave a ROESY correlation with $\delta_H$ 1.78 indicating a co-facial relationship of the benzoyl ester functionality with the methyl groups.

Compound C: White amorphous solid; $[\alpha]^{25}_D$ −199.23 (c 0.462 MeOH); $\lambda_{max}$ (log ε) 225 (4.3), 275 (3.0) and 345 nm (2.6); $^1H$ and $^{13}C$ NMR see Table 1; IR (CHCl$_3$) 3510, 1708, 1693, 1635, 1600 and 873 cm$^{-1}$; LREIMS m/z 436 [M]$^+$, 299, 122, 105 and 81; HREIMS gave m/z 436.2245 (calculated for $C_{27}H_{32}O_5$, 436.2250).

Figure 8:
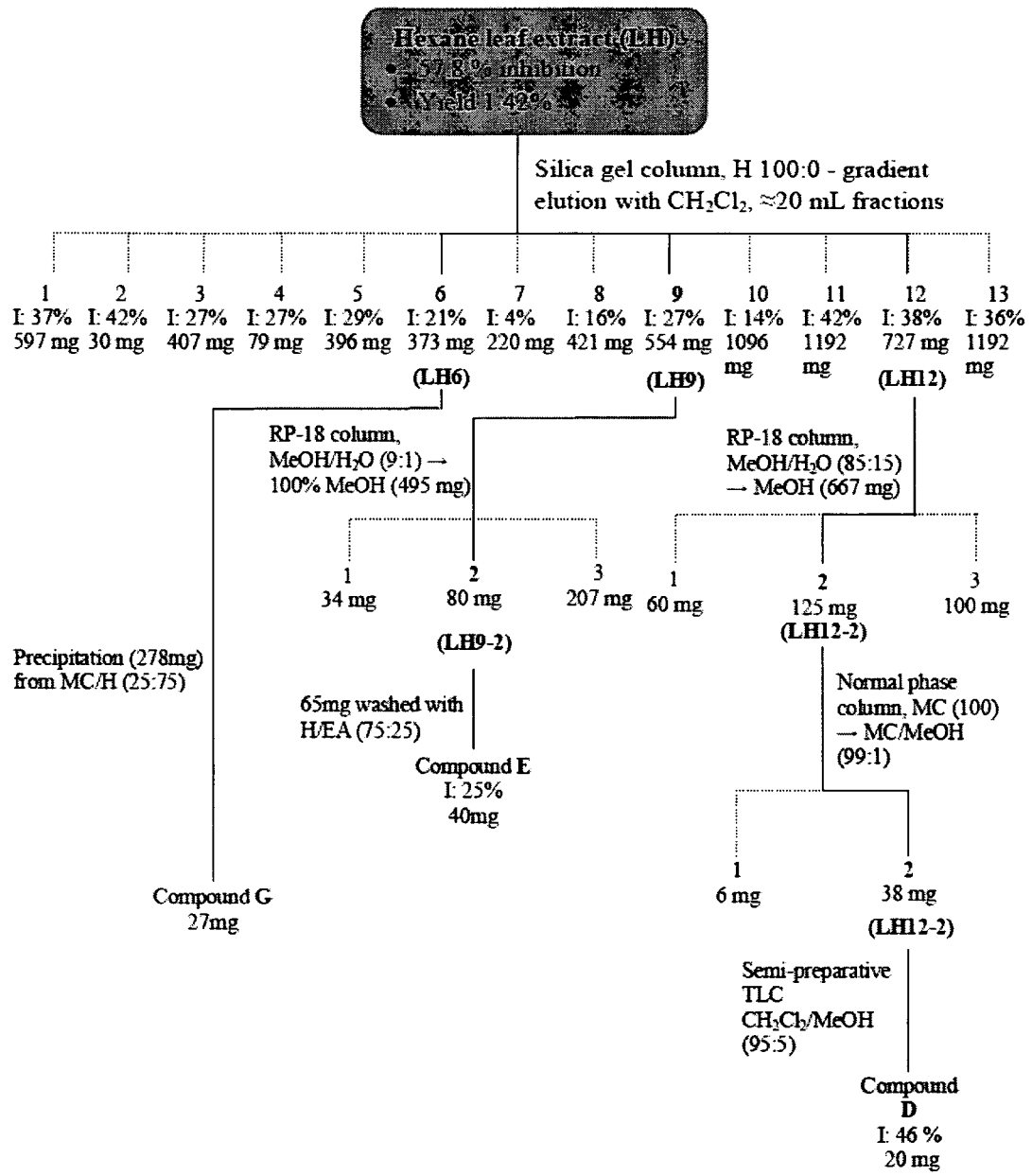
FIG. 8 shows a chart of the fractionation of a hexane leaf extract from Dodonaea polyandra leaves, the yield of the fractions and the inhibitory activity of the fractions. The chart also shows the purification of compounds from the extract, the yield of the compounds and the inhibitory activity of two of the compounds (compounds D and E).

FIG. 8 shows a chart of the further fractionation and purification of compounds from the LH extract fractions. Purification of Fr-LH9 was conducted in an identical manner to Fr-LH11 using low-pressure reverse phase (C18) column chromatography (Ø 30 mm, 150 mm packing height) with 90% MeOH/$H_2O$ isocratic elution. The fraction also contained a major green/blue spot with an Rf different to that of compound C obtained from Fr-LH11.3. The reverse phase column separation gave three fractions with Fr-LH9.2 containing the green/blue spot. During the preparation of a sample of Fr-LH9.2 for normal phase HPLC purification it was observed that the majority the sample was not soluble in the dissolvent being used (hexane/ethyl acetate (8:2)). The yellow colour of the sample moved into solution, with a white solid remaining at the bottom of the vial. Based on this observation a larger portion of the sample (65 mg) was carefully washed with cold hexane/ethyl acetate (8:2). The supernatant was withdrawn using a glass pasteur pipette and the process was repeated several times, leaving a white amorphous solid following evaporation of remaining solvent. Development of a sample applied to normal phase TLC revealed a single blue/green spot.

Figure 9:
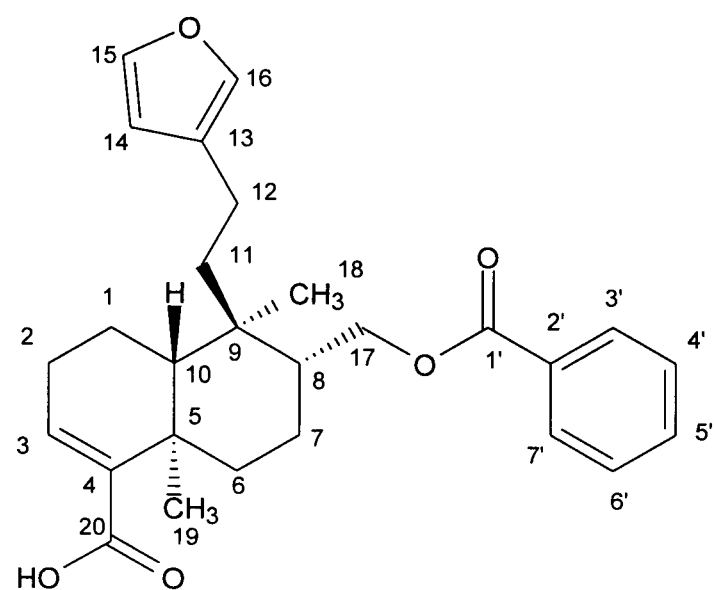
FIG. 9a shows the chemical structure of compound D isolated and tested for inhibitory activity from FIG. 8.
FIG. 9b shows the chemical structure of compound E isolated and tested for inhibitory activity from FIG. 8.

Completion of the washing process yielded 40 mg of compound E (FIG. 8). The chemical structure of compound E is shown in FIG. 9b.

Compound E was isolated as a white amorphous solid. The molecular formula was determined to be $C_{27}H_{32}O_5$ by high-resolution EI mass spectrometry (HREIMS) with the molecular ion peak at m/z 436.2246 (calcd for $C_{27}H_{32}O_5$, 436.2250). This suggested that the compound contained 12 degrees of unsaturation. The IR spectrum displayed strong absorption bands for a hydroxyl (3065 $cm^{-1}$), an ester carbonyl (1714 $cm^{-1}$), a conjugated carboxylic acid carbonyl (1681 $cm^{-1}$), alkene (1630 $cm^{-1}$) and furan (873 $cm^{-1}$) functionalities. The $^{13}C$ and DEPT spectra indicated the presence of 25 carbon resonances, two of which were methyl carbons ($\delta_C$ 20.5 and 19.2). Resonances for 7 methylene carbons ($\delta_C$ 66.6, 38.9, 35.2, 27.4, 22.4, 18.3 and 17.0), 2 $sp^3$ methine carbons ($\delta_C$ 46.7 and 41.0) and 9 $sp^2$ methine carbons ($\delta_C$ 142.8, 140.5, 138.6, 132.9, 129.5, 128.3, 111.0) were observed (the signals at $\delta_C$ 129.5 and 128.3 were tentatively ascribed to 2 pairs of equivalent carbons on the basis of signal intensities). In total, 7 quaternary carbons were accounted for consisting of 2 carbonyl carbons ($\delta_C$ 171.1 and 166.7), 3 $sp^2$ hybridized carbons ($\delta_C$ 141.0, 130.4 and 125.1) and 2 $sp^3$ carbons ($\delta_C$ 38.4 and 37.4). Eight of the 12 degrees of unsaturation could be attributed to the presence of 14 $sp^2$ carbon centres (comprising 2 carbonyl groups and 6 carbon-carbon double bonds) suggesting that the remaining degrees of unsaturation were due to the existence of four rings in the structure.

The $^1H$ NMR spectrum of compound E (Table 1) showed resonances for five aromatic protons ($\delta_H$ 8.00, dd, J=8.3, 1.3 Hz (2H); 7.54, tt, J=7.3, 1.3 Hz; 7.42, dd, J=8.3, 7.3 Hz (2H)), three furanyl protons ($\delta_H$ 7.33, t, J=1.7 Hz; 7.19, dd, J=1.7, 0.9 Hz; 6.27, dd, J=1.7, 0.9 Hz), a vinylic proton ($\delta_H$ 6.89, dd, J=4.8, 2.7 Hz), non-equivalent oxymethylene group ($\delta_H$ 4.52, dd, J=11.2, 4.5 Hz; 4.06, dd, 11.2, 8.0 Hz), two methyl singlets ($\delta_H$ 1.31, s; 0.92, s) and two methine signals ($\delta_H$ 1.96, m; 1.47, d, J=12.6).

In the COSY spectrum, the aromatic proton $\delta_H$ 8.00 ($\delta_C$ 129.5) coupled with $\delta_H$ 7.42 ($\delta_C$ 128.3) which further coupled to $\delta_H$ 7.54 ($\delta_C$ 132.9). Given the integration of $\delta_H$ 8.00 and $\delta_H$ 7.42, this suggested the presence of a monosubstituted six-membered aromatic ring. The furanyl protons $\delta_H$ 7.33 and $\delta_H$ 6.27 showed a COSY correlation. A third furan proton $\delta_H$ 7.19 did not give COSY correlations with other furanyl protons. This indicated a β-substituted furan moiety within the structure.

HMBC correlations confirmed the substitution pattern of aromatic protons ($\delta_H$ 8.00, 7.54, 7.42) while $\delta_H$ 8.00 correlated with an $sp^2$ carbon ($\delta_C$ 166.7) characteristic of an ester carbonyl. In addition, the oxymethylene protons ($\delta_H$ 4.52, 4.06) also correlated with $\delta_C$ 166.7, indicating compound 1 contained a benzoyl ester functionality.

The remaining resonances ($\delta_H$ 2.56, dt, J=13.2, 3.4 Hz; 1.20, dt, 13.4, 3.6 Hz), ($\delta_H$ 2.47, ddd, J=14.4, 12.2, 4.4 Hz; 2.25, m), ($\delta_H$ 2.36, dt, J=19.6, 4.8 Hz; 2.20, m), ($\delta_H$ 1.83, m; 1.61, dq, J=13.4, 3.4 Hz), ($\delta_H$ 1.73, m; 1.51, m) and ($\delta_H$ 1.78, m) were consistent with methylene protons of a fused cyclic ring system typical of clerodane diterpenoid compounds.

The methine proton $\delta_H$ 1.96 (attached to $\delta_C$ 41.0) showed a COSY relationship with the oxymethylene protons $\delta_H$ 4.52 & 4.06 and methylene protons $\delta_H$ 1.83 & 1.61. The same methylene protons showed COSY correlations to $\delta_H$ 2.56 & 1.20 (attached to $\delta_C$ 35.2). The methyl protons ($\delta_H$ 0.92) showed HMBC correlations to the methine carbon $\delta_C$ 41.0 and a quaternary $sp^3$ carbon $\delta_C$ 38.4. The second methyl group ($\delta_C$ 1.31) showed HMBC correlations to $\delta_C$ 35.2, the quaternary $sp^3$ carbon $\delta_C$ 37.4 and an $sp^2$ hybridized carbon ($\delta_C$ 141.0). The methine proton $\delta_H$ 1.47 gave HMBC correlations with $\delta_C$ 37.4 and methyl carbon $\delta_C$ 20.5. This suggested $\delta_H$ 1.47 was positioned adjacent to the methyl group attached to $\delta_C$ 37.4.

The vinylic signal $\delta_H$ 6.89 showed COSY correlations with methylene protons $\delta_H$ 2.36 & 2.20 and these also coupled with non-identical methylene protons $\delta_H$ 1.73 & 1.51. Furthermore, $\delta_H$ 1.73 & 1.51 coupled to $\delta_H$ 1.47 in the COSY spectrum. A HMBC correlation was observed for $\delta_H$ 2.36 & 2.20 to the vinylic carbon $\delta_C$ 141.0.

The remaining resonances in the $^1H$ and $^{13}C$ spectra which included methylene protons $\delta_H$ 2.47 & 2.25 ($\delta_C$ 18.3) showed HMBC correlations to an $sp^2$ carbon $\delta_C$ 125.1 and furan $sp^2$ methine carbon $\delta_C$ 138.6. Two equivalent methylene protons $\delta_H$ 1.78 gave COSY correlations to non-equivalent methylene protons $\delta_H$ 2.47 & 2.25 and HMBC correlation to quaternary carbon $\delta_C$ 38.4 to which the methyl group ($\delta_H$ 0.92, $\delta_C$ 19.2) was established to be attached. This confirmed the presence of a furanyl functionality containing an ethyl linkage between the β-carbon of the furan ring and quaternary carbon $\delta_C$ 38.4 (C-9). Further confirmation of this fragment was provided by the UV absorption at 225 nm, the IR absorption at 873 $cm^{-1}$ and the presence of significant ions at m/z 81 ($C_5H_5O$) and 95 ($C_6H_7O$) in the EIMS. These cleavages in the mass spectrum are commonly seen in clerodane diterpenoids containing a furanyl group with an unsubstituted side chain.

A substructure with a formula mass of 391 amu was obtained having exhausted the available data from NMR, meaning there remained an unaccounted mass of 45 amu. This indicated the presence of a carboxylic acid group, which was supported by a peak in the $^{13}C$ NMR spectrum at $\delta_C$ 171.1 as well as an —OH stretch at 3065 $cm^{-1}$ in the IR spectrum. Based on the three bond HMBC correlations of the vinylic proton $\delta_H$ 6.77 to $\delta_C$ 171.1, the carboxylic acid was positioned attached to the quaternary carbon $\delta_C$ 141.0. NMR spectral data for similar compounds as reported in the literature further supported this positioning (Ahmad, V. U.; Khan, A.; Farooq, U.; Kousar, F.; Saleha Suleman Khan; Nawaz, S. A.; Abbasi, M. A.; Choudhary, M. I., Three New Cholinesterase-Inhibiting cis-Clerodane Diterpenoids from *Otostegia limbata*. Chemical and Pharmaceutical Bulletin 2005, 53, (4), 378-381; Huang, Z.; Jiang, M.; Zhou, Z.; Xua, D., Two new clerodane diterpenes from *Dodonaea viscosa*. Zeitschrift fur Naturforschung: Section B Journal of Chemical Sciences 2010, 65, (1), 83-86). Given the above data, the structure of this new compound was established to be the clerodane furanoditerpenoid 1, 15,16-epoxy-8(α)-(benzoyloxy)methyl-cleroda-3,13(16), 14-trien-18-oic acid.

The assignment of relative configuration of the stereocentres of compound E was carried out using ROESY data as well as information obtained from previously isolated clerodane diterpenoids from *Dodonaea* spp. Clerodane diterpenoids previously isolated from the genus *Dodonaea* having a C-3-C-4 double bond, typically contain (but not always) a trans arrangement at the ring junction (Ghisalberti, E. L., Ethnopharmacology and Phytochemistry of *Dodonaea* species. Fitoterapia 1998, 69, 99-113; Huang, Z.; Jiang, M.; Zhou, Z.; Xua, D., Two new clerodane diterpenes from *Dodonaea viscosa*. Zeitschrift fur Naturforschung: Section B Journal of Chemical Sciences 2010, 65, (1), 83-86). The Me-19 may also serve as a basis for determining the conformation of the A/B ring junction—for trans fusion the chemical shift of C-19 methyl is typically in the range of ~$\delta_C$ 11-19 ppm, in contrast to cis fusion where the C-19 methyl resonance is observed to be ~$\delta$ 5-10 ppm higher (typically $\delta_C$ 25 ppm) (Manabe, S.; Nishino, C., Stereochemistry of cis-clerodane diterpenes. *Tetrahedron* 1986, 42, (13), 3461-3470). In this case, the C-19 methyl resonance is observed at $\delta_C$ 20.5 ppm, which is on the lower end of the chemical shift range which may indicate a cis orientation (although the shift is slightly out of the usually observed range). However, the Me-19 resonance of a structurally related compound (−)-hardwickiic acid, whose x-ray crystal structure has been determined, also displays a slightly higher chemical shift for the trans Me-19 ($\delta$ 20.6) (Santos, A. G. d.; Perez, C. C.; Tininis, A. G.; Bolzani, V. d. S.; Cavalheiro, A. J., Clerodane Diterpenes from Leaves of *Casearia sylvestris* Swartz. *Química Nova* 2007, 30, (5), 1100-1103; Chaichantipyuth, C.; Muangsin, N.; Chaichit, N.; Roengsumran, S.; Petsom, A.; Watanabe, T.; Ishikawa, T., Crystal structure of (−)-hardwickiic acid, $C_{19}H_{27}OCOOH$. *Zeitschrift für Kristallographie* 2004, 219, 111-113). In addition the chemical shift of Me-($\delta$ 19.2) which is typical of trans clerodanes, supported a trans ring junction in compound E. From ROESY data, the C-19 methyl group ($\delta_H$ 1.31) showed correlation with the C-20 methyl ($\delta_H$ 0.92) which in turn showed correlation with the oxymethylene protons of C-17 ($\delta_H$ 4.5 & 4.06). These observations, together with other ROESY correlations, established the relative configurations for carbons C-1, C-5, C-8 and C-9.

Compound E: White amorphous solid; $[\alpha]^{20}_D$ −69.54 (c 0.805 MeOH); $\lambda_{max}$ (log $\epsilon$) 225 (4.4) and 275 nm (3.0); IR ($CHCl_3$) 3065, 1714, 1681, 1630, 1602, 1276 and 873 $cm^{-1}$; $^1H$ and $^{13}C$ NMR see Table 1; LREIMS m/z 436 $[M]^+$, 219, 125, 105, 95 and 81; HREIMS m/z 436.2246 (calculated for $C_{27}H_{32}O_5$, 436.2250).

Figure 10:
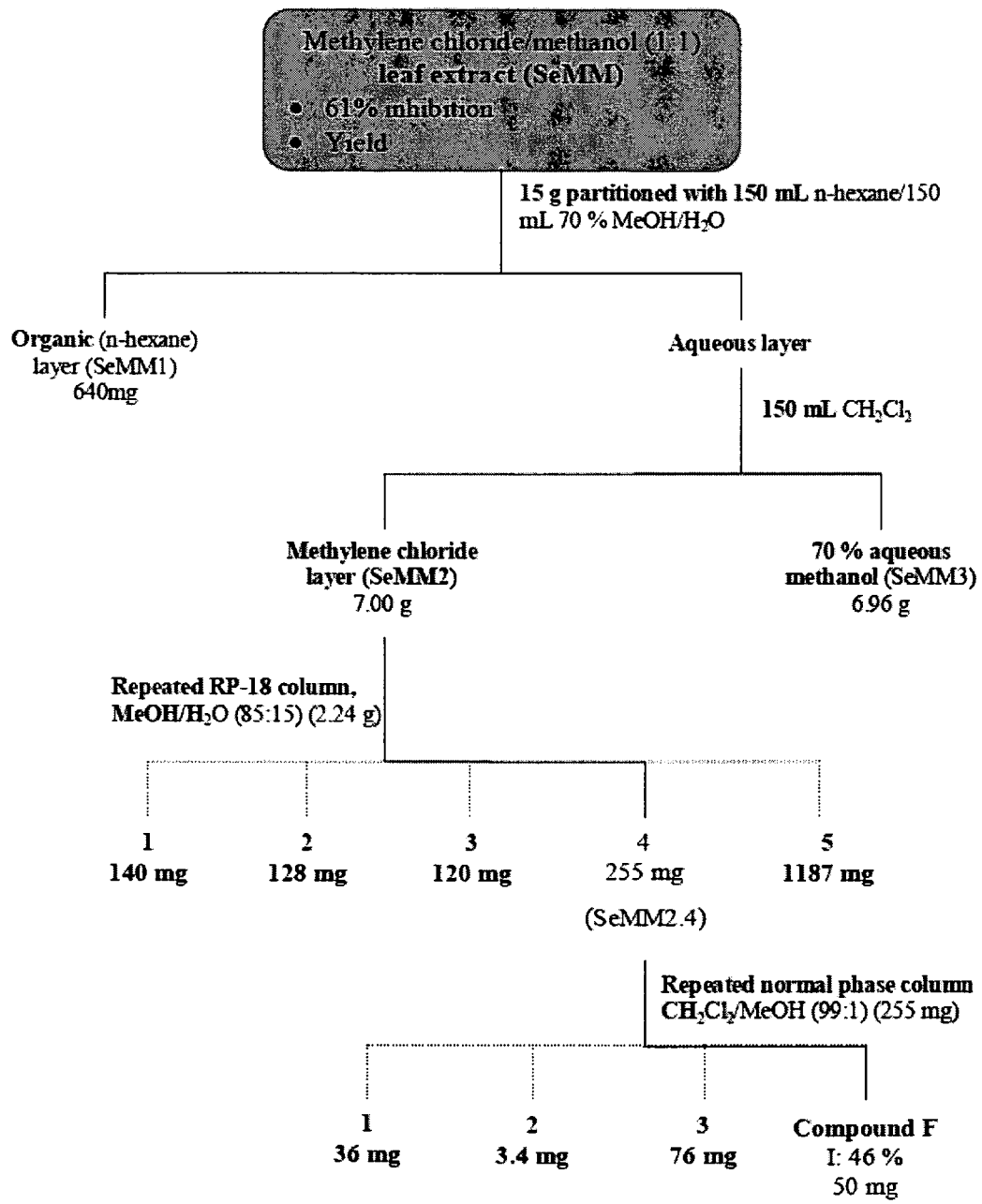
FIG. 10 shows a chart of the fractionation of a methylene chloride/methanol (1:1) leaf extract from Dodonaea polyandra leaves and the yield of the fractions. The chart also shows the purification of compounds from the extract, the yield of the compounds and the inhibitory activity of one of the compounds (compound F).
Figure 11:
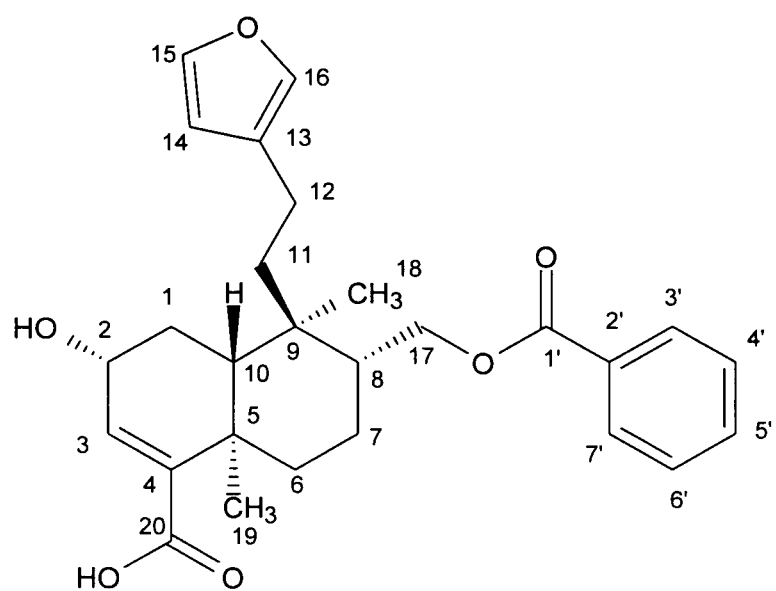
FIG. 11 shows the chemical structure of compound F isolated and tested for inhibitory activity from FIG. 10.

An initial clean-up step of the SeMM extract was conducted by dissolving 15 g of SeMM extract in 150 mL 70% $MeOH/H_2O$ and partitioning between 150 mL n-hexane. The flow chart shown in FIG. 10 summarises the processes involved. The aqueous layer was retained and subsequently extracted with 150 mL $CH_2Cl_2$. The $CH_2Cl_2$ layer which contained the component of interest was evaporated on a rotavap at 37° C. under reduced pressure to give Fr-SeMMMc (7.00 g). Fraction SeMM2 (2.24 g) was subjected to repeated low-pressure reverse phase (C18) column chromatography (Ø 30 mm, 150 mm packing height) under isocratic elution with 85% MeOH/H2O. The separation was monitored by normal phase TLC until the blue/green spot of interest had eluted from the column. The column was washed with MeOH followed by isopropanol to remove remaining components from the column. Five fractions (SeMM2.1-SeMM2.5) were pooled together on the basis of TLC analysis with Fr-SeMM2.4 containing the blue/green spot. The SeMM2.4 fraction (255 mg) was purified further under low pressure normal phase conditions ($\phi$ 10 mm, packing height 240 mm) and CH2Cl2/MeOH (99:1) eluent. This process was repeated twice to yield compound F (50 mg) as a white amorphous solid. The chemical structure of compound F is shown in FIG. 11.

It was revealed from analysis of the NMR spectroscopic data of compound F that this compound was also a clerodane furanoditerpenoid with distinct similarities to that of compound E. The molecular formula was determined to be $C_{27}H_{32}O_6$ from the M-H peak m/z 451.2123 (calcd for $C_{27}H_{31}O_6$, 451.2121). Resonances for furan protons $\delta_H$ 7.31 (t, J=1.7 Hz), 7.19 (dd, J=1.7, 0.9 Hz) and 6.28 (dd, J=1.7, 0.9 Hz) indicated this compound also contained a β-furan moiety. It was further established that the ethyl furan group was attached to the same position as in compound E. Almost identical resonances were observed for aromatic protons in this compound similar to those established in compound E ($\delta_H$ 8.00, dd, J=8.3, 1.3 Hz; 7.55, tt, J=7.4, 1.4 Hz; 7.41, dd, J=8.3, 7.4 Hz)). The aromatic protons $\delta_H$ 8.00 also showed identical HMBC correlations to a carbonyl compound ($\delta_C$ 166.7) as seen in compound E. In addition, similar resonances were observed for two non-identical oxymethylene protons ($\delta_H$ 4.53, dd, J=11.1, 7.6; 4.08 Hz), dd, J=11.1, 7.8 Hz) attached to $\delta_C$ 66.4. This clearly suggested that this compound also featured a benzoyl ester functionality. Further confirmation was provided by HMBC data which showed correlations between oxymethylene protons ($\delta_H$ 4.53 & 4.08) and carbons $\delta_C$ 40.9, 38.1 and 22.3 indicating the ester was attached at the same position (C-8) as in compound E. The most notable difference in the $^1H$ NMR spectrum of compound F was an oxymethine proton ($\delta_H$ 4.39, dt, J=4.5, 1.4 Hz), which showed strong COSY correlations with the vinylic proton ($\delta_H$ 6.27, dd, J=4.5, 1.4 Hz) that was established to be in the same position at C-3 ($\delta_C$ 136.5) as seen in compound E. This indicated the presence of a hydroxyl functionality at this position in comparison to E. Although the existence of a hydroxyl group was not apparent from the $^1H$ NMR or IR spectrum, the total number of carbons and MS accurate mass strongly supported this proposition. The oxymethine proton at $\delta_H$ 4.39 also showed COSY correlation with chemically non-equivalent methylene protons ($\delta_H$ 1.96, m; 1.76, m) at position C-1 ($\delta_C$ 26.8). An unassigned carboxylic acid carbon ($\delta_C$ 171.0) was also found to occupy attachment to the C-4 vinylic carbon ($\delta_C$ 143.9) as determined for compound E based upon HMBC correlations between the vinylic proton at C-3 and the carbon of $\delta_C$ 171.0. Given the above data, the structure of this new compound was established to be the clerodane diterpenoid F, 15,16-epoxy-8($\alpha$)-(benzoyloxy)methyl-3 ($\alpha$)-hydroxy-cleroda-3,13(16), 14-trien-18-oic acid.

The assignment of the relative configuration at C-10 in compound F was assumed to be the same as that of compound E. The relative configuration of the remaining stereocentres was established using ROESY NMR experiments and were the same as those determined for compound E. Methyl protons ($\delta_H$ 1.27) of the methyl group attached to C-5 showed a strong ROESY correlation with the second methyl group attached to C-9. In addition, the same methyl protons strongly correlated with the oxymethylene protons ($\delta_H$ 4.53, 4.08) indicating the spatial proximity of these groups. Strong ROESY correlations between the methine proton at C-10 ($\delta_H$ 1.75) and the oxymethine proton at C-2 ($\delta_H$ 4.39) together with other ROESY correlations, established the relative configurations for carbons C-2, C-5, C-8, C-9 and C-10.

Compound F: White crystalline needles; M.p. 81-83° C.; $[\alpha]^{20}_D$ −75.36 (c 0.836 MeOH); $\lambda_{max}$ (log $\epsilon$) 225 (4.3), 270 (3.0) and 345 nm (2.7); IR ($CHCl_3$) 3090, 1712, 1692, 1633, 1602, 1278, and 873 $cm^{-1}$; $^1H$ and $^{13}C$ NMR see Table 1; LRAPCI m/z 451 $[M-H]^-$; HRAPCI m/z 451.2123 (calculated for $C_{27}H_{31}O_6$, 451.2121).

The isolation of compounds from the n-hexane crude leaf extract of *D. polyandra* was based on a partial activity-guided fractionation process. The rationale for this was due to the in vivo approach used to measure pharmacological activity. The statistically meaningful data obtained from testing semi-purified fractions and the chemical simplicity of these fractions meant that it was probable the activity was due to the most abundant component(s). Therefore further separation of the most active semi-purified fractions was guided based on the most prominent spots observed on TLC.

Example 9

Fractionation of *D. polyandra* Leaf Extract

An extract of *D. polyandra* stems with $CH_2Cl_2$/MeOH (1:1) was prepared using the same procedure as described above for leaf extract preparation. The extract (DPS) yield was 34.9 g (9.8%) and was further purified by liquid/liquid partitioning between $CH_2Cl_2$ and 70% aqueous methanol (350 mL each, 700 mL total). The organic layer was removed, dried and evaporated at 40-42° C. giving a yield of 14.4 g. An initial separation of 10.1 g of the $CH_2Cl_2$ fraction (DPS1) was carried out using normal phase glass column chromatography eluting with n-hexane/$CH_2Cl_2$ with increasing amounts of $CH_2Cl_2$, ceasing with $CH_2Cl_2$/MeOH (95/5). Eluant was collected (15 mL samples) and grouped into three major fractions based on the TLC profiles of the samples.

Figure 12:
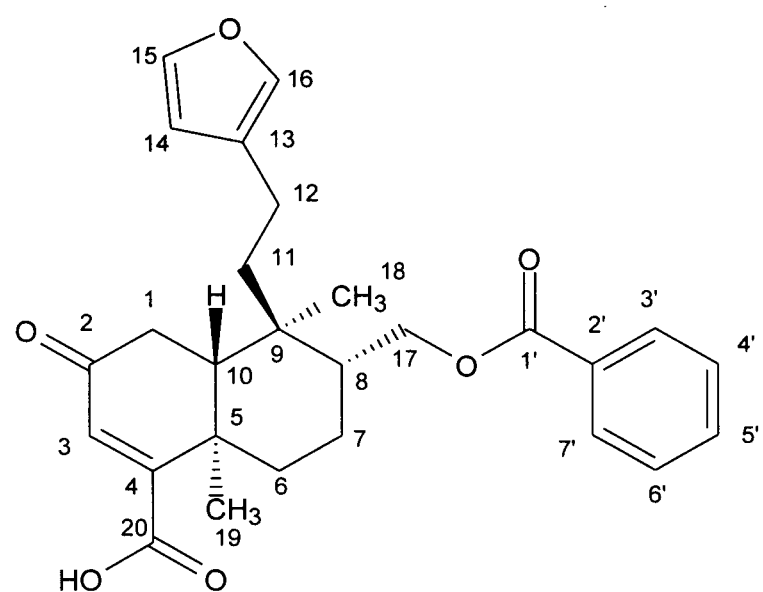
FIG. 12 shows the chemical structure of compound H isolated and tested for inhibitory activity.

Fraction DPS1A (4.1 g) was separated under reverse phase conditions eluting with 75% aqueous methanol with increasing amounts of methanol to afford 3 major fractions (DPS1A1, DPS1A2 and DPS1A3). Fraction DPS1A1 (685 mg) was passed through a Sephadex LH-20 column eluting with $CH_2Cl_2$/MeOH (3:1) giving two fractions (DPS1A1a and DPS1A1b). Fraction DPS1A1a (40 mg) was separated using normal phase preparative TLC ($CH_2Cl_2$/MeOH 95/5). The region of interest was cut out and the component of interest recovered by passing ethyl acetate through the sample which had been placed into a miniature glass column. Upon drying of the sample under nitrogen, 1 mg of compound H was obtained as an off-white solid. The chemical structure of compound H is shown in FIG. 12.

Compound H was isolated as an off-white amorphous solid with the molecular formula $C_{27}H_{30}O_6$ which was determined from the molecular ion $[M]^+$ peak at m/z 450.2041 (calcd for $C_{27}H_{30}O_6$, 450.2042). A two proton difference between this compound and F indicated the presence of an additional degree of unsaturation. The $^1H$ NMR spectrum of compound H (Table 1) was almost identical to that of compound F with one exception being the absence of the oxymethine proton that was observed at $\delta_H$ 4.39 in the $^1H$ NMR spectrum of compound F. Similarly the $^{13}C$ NMR spectrum showed distinct similarities with that of compound F, however a significant peak at $\delta_C$ 200.2 which was not present in the spectrum of F suggested that a ketone functional group was present in compound H instead of the secondary alcohol observed in compound F. The position of this group was determined to be at C-2 as indicated by HMBC correlations observed between methylene protons $\delta_H$ 2.51 (C-1) and methine proton $\delta_H$ 2.09 (C-10) to carbon $\delta_C$ 200.2. Given the minor structural differences described above the structure of this new compound H was established as 15,16-epoxy-8(α)-(benzoyloxy)methyl-2-oxo-cleroda-3,13(16), 14-trien-18-oic acid.

The assignment of relative configuration to stereocentres used similar evidence as previously described. Both methyl groups ($\delta_H$ 1.45, $\delta_C$ 18.7 & $\delta_H$ 1.10, $\delta_C$ 18.7) showed ROESY correlations, however neither correlated with the methine proton $\delta_H$ 2.09, again suggesting a trans configuration at the ring junction. Proton $\delta_H$ 2.09 and $\delta_H$ 2.01 showed a ROESY correlation indicating that the benzoyl ester moiety was orientated in the same position as for compounds E and F. This established the relative configurations of C-5, C-8, C9 and C-10 as being the same as in compounds E and F.

Compound H: Off-white solid; LREIMS m/z 450 $[M]^+$, 417, 234, 189, 105, 95, 81, 77; $^1H$ and $^{13}C$ NMR see Table 1; HREIMS m/z 450.2041 (calculated for $C_{27}H_{30}O_6$, 450.2042).

TABLE 1

NMR Spectroscopic Data (600 MHz) for compounds C, E, F and H

| pos | $E^{a,b}$ $\delta_C$, multi. | $\delta_H$ (J in Hz) | $F^{a,b}$ $\delta_C$, multi. | $\delta_H$ (J in Hz) | $H^{a,b}$ $\delta_C$, multi. | $\delta_H$ (J in Hz) | $C^{a,b}$ $\delta_C$, multi. | $\delta_H$ (J in Hz) |
|---|---|---|---|---|---|---|---|---|
| 1 | 17.0, $CH_2$ | b 1.73 m; a 1.51 m | 26.8, $CH_2$ | b 1.96 m; a 1.76 m | 34.6, $CH_2$ | 2.51 d (8.8) | 24.8, $CH_2$ | b 1.95 ddd (15.0 12.8, 5.0); a 2.02 dq (15.0, 1.8) |
| 2 | 27.4, $CH_2$ | a 2.36 dt (19.6, 4.8); b 2.20 m | 66.2, CH | 4.39 dt (4.5, 1.4) | 200.2, C | | 67.6, CH | 5.65 dt (4.8, 1.4) |
| 3 | 140.5, CH | 6.89 dd (4.8, 2.7) | 136.5, CH | 6.72 dd (4.5, 1.4) | 130.2, CH | 6.41bs | 132.7, CH | 6.77 dd (4.4, 1.4) |
| 4 | 141.0, C | | 143.9, C | | 142.9, C | | 146.4, C | |
| 5 | 37.4, C | | 38.0, C | | 38.5, C | | 38.0, C | |
| 6 | 35.2, $CH_2$ | a 2.56 dt (13.2, 3.4); b 1.20 dt (13.4, 3.6) | 34.7, $CH_2$ | a 2.46 m; b 1.25 dt (13.3, 3.8) | 34.2, $CH_2$ | a 2.38 dt (12.6, 3.0); b 1.44 m | 35.3, $CH_2$ | a 2.36 m; b 1.30 dt (12.6, 4.1) |
| 7 | 22.4, $CH_2$ | b 1.83 m; a 1.61 dq (13.4, 3.4) | 22.3, $CH_2$ | b 1.85 m; a 1.63 dq (13.2, 3.6) | 21.8, $CH_2$ | b 1.93 m; a 1.71m | 27.1, $CH_2$ | b 1.48 m; a 1.51 m |
| 8 | 41.0, CH | 1.96 m | 40.9, CH | 2.01 m | 40.7, CH | 2.01 m | 36.1, CH | 1.64 m |
| 9 | 38.4, C | | 38.1, C | | 38.3 | | 38.5, C | |
| 10 | 46.7, CH | 1.47 d (12.6) | 41.4, CH | b 1.75 m | 45.6, CH | 2.09 t (8.8) | 42.1, CH | 1.78 dd (12.8, 2.0) |
| 11 | 38.9, $CH_2$ | 1.78 m | 38.9, $CH_2$ | 1.77 m | 38.3, $CH_2$ | 1.92 m; 1.71 m | 38.3, $CH_2$ | 1.57 m |
| 12 | 18.3, $CH_2$ | 2.47 ddd (14.4, 12.2, 4.8); 2.25 m | 17.8, $CH_2$ | 2.56 m; 2.44 m | 18.1 $CH_2$ | 2.49 m; 2.23m | 17.7, $CH_2$ | 2.38 m; 2.30 m |
| 13 | 125.1, C | | 125.2, C | | 124.3, C | | 125.0, C | |
| 14 | 111.0, CH | 6.27 dd (1.7, 0.9) | 111.1, CH | 6.28 dd (1.7, 0.9) | 110.8, CH | 6.25 dd (1.7, 0.9) | 110.7, CH | 6.00 dd (1.7, 0.9) |
| 15 | 142.8, CH | 7.33 t (1.7) | 142.6, CH | 7.31 t (1.7) | 142.9 CH | 7.32 t (1.7) | 142.5, CH | 7.20 t (1.7) |
| 16 | 138.6, CH | 7.19 dd (1.7, 0.9) | 138.6, CH | 7.19 dd (1.7, 0.9) | 138.7 CH | 7.18 bs | 138.3, CH | 6.76 dd (1.7, 0.9) |
| 17 | 66.6, $CH_2$ | 4.52 dd (11.2, 4.5); 4.06 dd (11.2, 8.0) | 66.4, $CH_2$ | 4.53 dd (11.1, 4.6); 4.08 dd (11.1, 7.8) | 65.9, $CH_2$ | 4.54 dd (11.4, 4.8); 4.08 dd (11.4, 8.4) | 15.8, $CH_3$ | 0.86 d (6.6) |
| 18 | 171.1, C | | 171.0, C | | 168.5, C | | 171.1, C | |
| 19 | 20.5, $CH_3$ | 1.31 s | 18.8, $CH_3$ | 1.27 s | 18.7, $CH_3$ | 1.45 s | 18.9, $CH_3$ | 1.29 s |
| 20 | 19.2, $CH_3$ | 0.92 s | 19.2, $CH_3$ | 0.92 s | 18.7, $CH_3$ | 1.10 s | 18.0, $CH_3$ | 0.79 s |
| 1' | 166.7, C | | 166.7, C | | 166.6, C | | 165.9, C | |
| 2' | 130.4, C | | 130.3, C | | 130.1, C | | 129.9, C | |
| 3' | 129.5, CH | 8.00 dd (8.3, 1.3) | 129.5, CH | 8.00 dd (8.3, 1.4) | 129.5, CH | 8.00 dd (8.3, 1.3) | 129.7, CH | 8.01 dd (8.4, 1.3) |
| 4' | 128.3, CH | 7.42 dd (8.3, 7.3) | 128.4, CH | 7.41 dd (8.3, 7.4) | 128.4, CH | 7.42 dd (8.3, 7.4) | 128.4, CH | 7.37 dd (8.4, 7.4) |
| 5' | 132.9, CH | 7.54 tt (7.3, 1.3) | 132.9, CH | 7.55 tt (7.4, 1.4) | 133.0, CH | 7.56 tt (7.4, 1.3) | 133.2, CH | 7.53 tt (7.4, 1.3) |

TABLE 1-continued

NMR Spectroscopic Data (600 MHz) for compounds C, E, F and H

| | E[a,b] | | F[a,b] | | H[a,b] | | C[a,b] | |
|---|---|---|---|---|---|---|---|---|
| pos | $\delta_C$, multi. | $\delta_H$ (J in Hz) | $\delta_C$, multi. | $\delta_H$ (J in Hz) | $\delta_C$, multi. | $\delta_H$ (J in Hz) | $\delta_C$, multi. | $\delta_H$ (J in Hz) |
| 6' | 128.3, CH | 7.42 dd (8.3, 7.3) | 128.4, CH | 7.41 dd (8.3, 7.4) | 128.4, CH | 7.42 dd (8.3, 7.4) | 128.4, CH | 7.37 dd (8.4, 7.4) |
| 7' | 129.5, CH | 8.00 dd (8.3, 1.3) | 129.5, CH | 8.00 dd (8.3, 1.4) | 129.5, CH | 8.00 dd (8.3, 1.3) | 129.7, CH | 8.01 dd (8.4, 1.3) |

[a]CDCl$_3$ was used as solvent;
[b]No signals for OH observed in $^1$H NMR

Example 10

Semi-Purified Leaf Extracts of *D. polyandra* Inhibit Inflammation in the Mouse Oedema Model Semi-purified fractions LH1-LH13 prepared as per example 8 were used in the mouse oedema model to determine the anti-inflammatory effect of the fractions. As shown in FIG. 13, fractions LH11, LH12 and LH13 showed a significant average % inhibition oedema of 41.7, 37.6 and 35.6%, respectively when tested at 0.4 mg/ear.

Example 11

Compounds Purified from Leaf Extracts of *D. polyandra* Inhibit Inflammation in the Mouse Oedema Model Compounds C, E and F showed significant anti-inflammatory activity in a TPA-induced mouse ear oedema model with the most potent being C and F (the quantity of H obtained did not allow for testing to be conducted). Whilst compound E showed some significant level of activity when compared to TPA only control at the highest dose tested (1.83 μmol/ear, p<0.05), there was no observable effect at lower concentrations. Compound F showed a dose-response over the dose range 0.0055-1.77 μmol/ear. At 8 hrs post application, 0.22 μmol/ear dose gave a maximum of 70.2±10.0% (mean±SEM) inhibition with no improvement in activity observed for the two higher doses. Compound E showed equally potent activity as F with maximum inhibition of 76.4±7.3% achieved at a dose of 0.91 μmol, with activities comparable to the positive control betamethasone dipropionate (0.90 μmol/ear). However, the dose-response relationship of C was characterized by a U-shaped dose-response over the experimental range, featuring significant activities at low and high doses. The shape of this dose-response is actually rather common of immune system-related endpoints, however the significance of such phenomena is often ignored. Whilst a number of classes of compounds have been reported for inducing such dose-responses, steroids are noteworthy examples typically associated with having these effects (Calabrese, E. J., Hormetic Dose-Response Relationships in Immunology: Occurrence, Quantitative Features of the Dose Response, Mechanistic Foundations and Clinical Implications *Critical Reviews in Toxicology* 2005, 35, 89-295; Snijdewint, F. G.; Kapsenberg, M. L.; Wauben-Penris, P. J.; Bos, J. D., Corticosteroids class-dependently inhibit in vitro Th1- and Th2-type cytokine production. *Immunopharmacology* 1995, 29, 93-101). A further point of interest is that BALB/c mouse models (the type used in this investigation) are commonly associated with displaying these types of dose-responses.

Figure 14:
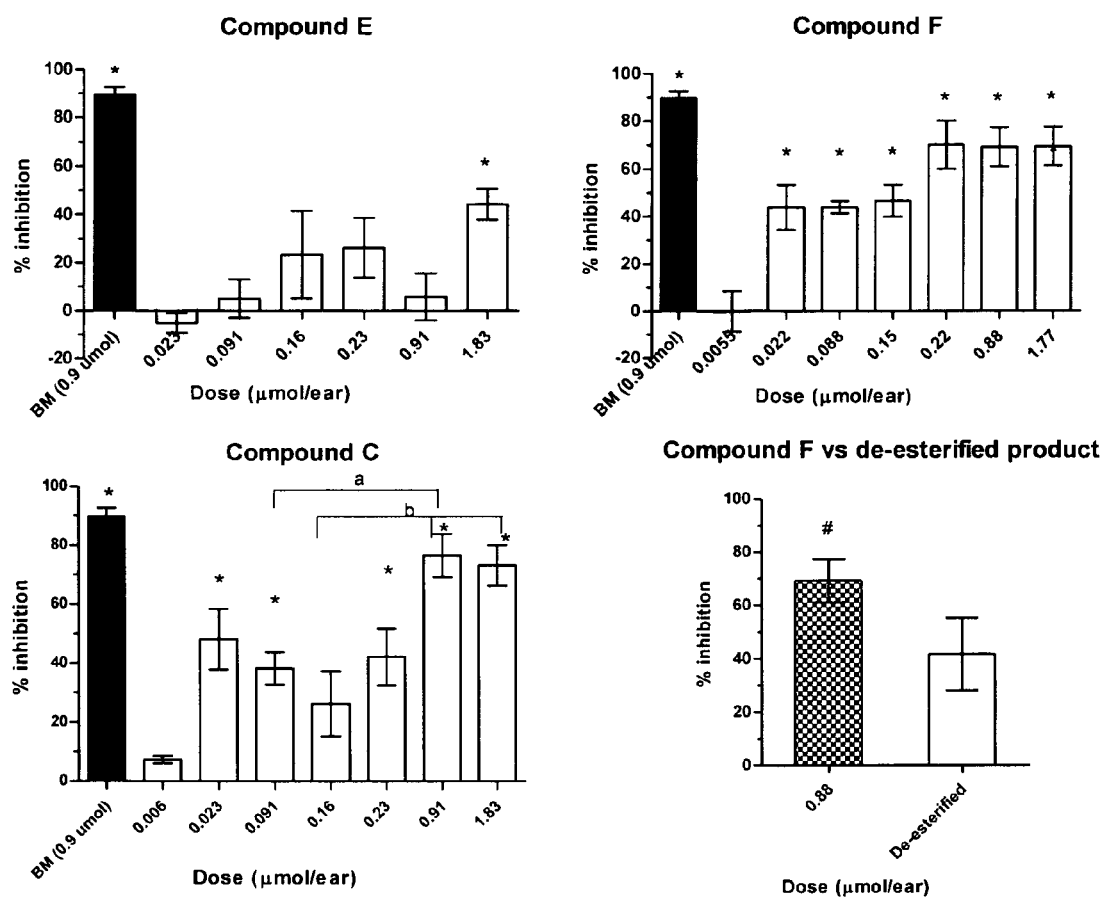
FIG. 14 shows graphical representations of dose-response characteristics of isolated compounds E, F and C and comparison of the activities between F and its de-esterified product in a TPA-induced mouse ear oedema model of inflammation. Doses presented are µmol/ear. Percentage inhibition data are presented as the mean±SEM (for E n=4, for F and C n≥6 for each treatment group, data calculated at t=8 hr)*p<0.05 compared to negative TPA control; a,b p<0.05 a statistically significant difference exists between treated groups of the same compound; #p<0.05 a statistically significant difference exists between compound F and its de-esterified product at a dose of 0.88 µmol/ear).
Figure 15:
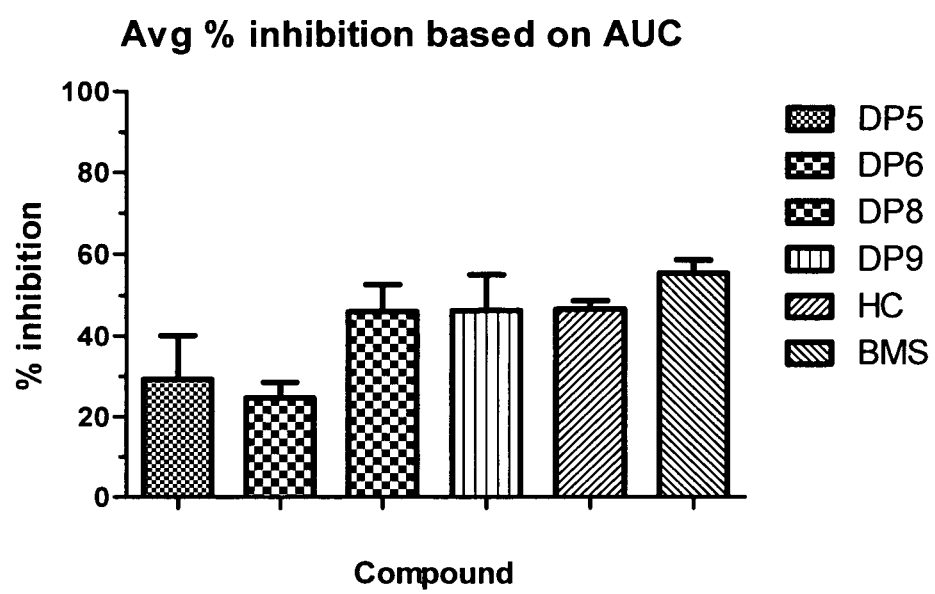
FIG. 15 shows a graph of the average percent inhibition of inflammation over 48 hours for compound C (DP5), compound D (DP9), compound E (DP6) and compound F (DP8) in the murine model of inflammation. Hydrocortisone (HC) and betamethasone dipropionate (BMS) were used as positive controls.
Figure 16:
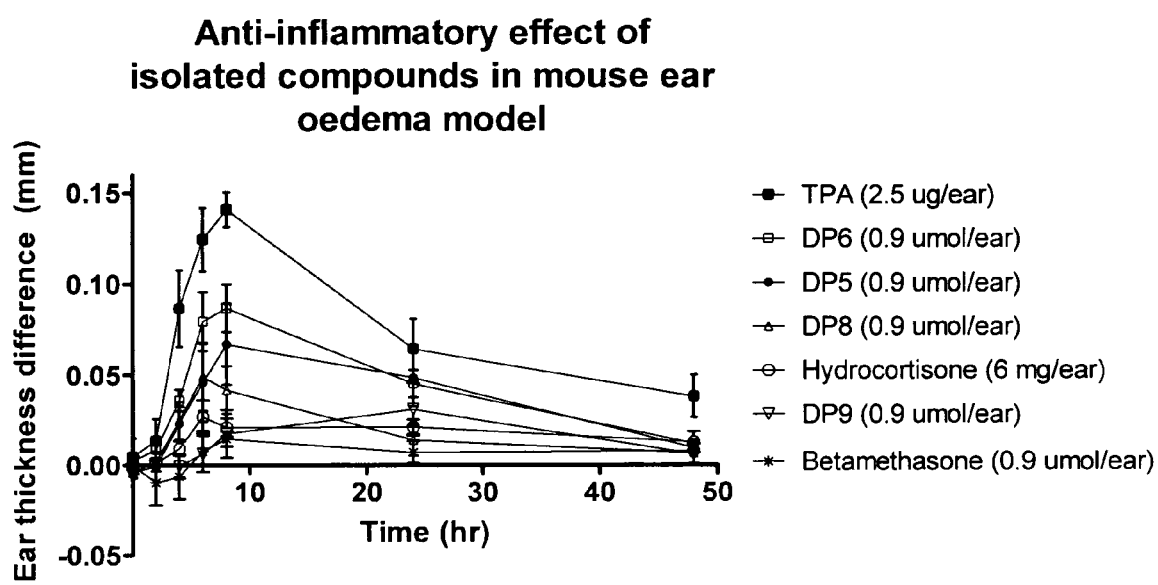
FIG. 16 shows a graph of the time course of the inflammation reduction by compound C (DP5), compound D (DP9), compound E (DP6) and compound F (DP8) in the murine model of inflammation. TPA was used as a negative control. Betamethasone was used as a positive control. The graph is interpreted as the TPA line being the maximum inflammatory response and any line beneath the TPA line being indicative of some level of anti-inflammation.

The inhibitory effects of the compounds are also shown in FIGS. 14 and 15.

Example 12

Alkaline Hydrolysis of Compound F—Effect of the Benzoyl Moiety on Anti-Inflammatory Activity To determine whether the benzoyl ester moiety was important for the observed activity, compound F was subjected to mild alkaline hydrolysis and subsequently tested in vivo.

Mild alkaline ester hydrolysis of compound F was carried out using a previously described method (Khurana, J. M.; Chauhan, S.; Bansal, G., Facile Hydrolysis of Esters with KOH-Methanol at Ambient Temperature. *Monatshefte für Chemie* 2004, 135, 83-87). Briefly, potassium hydroxide (Merck, Darmstadt) was reacted with the compound using a mol ratio of 3:1 in 100 μL methanol at 37° C. The progress of the reaction was monitored and terminated at 2 hr by addition of 300 μL water, followed by 100 μL of 1M HCl. The component of interest was recovered by liquid-liquid extraction with 500 μL $CH_2Cl_2$ and the organic layer subsequently removed from aqueous layer, dried over sodium sulphate and centrifuged (14,000 rpm for 5 min) to remove solid particulates. The dried organic layer containing the hydrolysed component of interest was purified by preparative TLC under normal phase conditions (92.5/7.5$CH_2Cl_2$/MeOH). The structure of the hydrolysis product was confirmed by NMR.

As shown in FIG. 13, removal of the benzoyl functional group significantly reduced (p<0.05) the ability of the compound to inhibit inflammation (oedema) in vivo.

Example 13

COX Inhibition Assays

Compounds C and F were tested for their ability to inhibit COX-1 and COX-2 enzyme activities using a COX fluorescent inhibitor screening assay kit (Cayman Chemical).

The COX inhibitor screening assay screens for both ovine COX-1 and human recombinant COX-2 for specific inhibitors. Neither compound C or F significantly affected COX-1 or COX-2 activities at concentrations regaining from 0.03 μM to 10 μM. This indicates that the inhibition of inflammation shown in the previous Examples is likely to be proceeding via a mechanism other than COX-1 and/or COX-2 inhibition.

Example 14

Topical Composition

A topical cream could be formed as follows. Stearyl alcohol (60 g) and USP olive oil (940 g) can be separately heated to 80° C. While at 80° C., the stearyl alcohol can be added to the preheated olive oil. Glycerin (20 g), tri-stearin (20 g), and an antioxidant (1 g) can then be added by agitation. The active compound (1 g) can then be added and the mixture poured into containers and allowed to cool spontaneously to form a semi solid mixture.

Those skilled in the art will appreciate that the invention described herein is susceptible to variations and modifications other than those specifically described. It is to be understood that the invention includes all such variations and modifications. The invention also includes all of the steps, features, compositions and compounds referred to, or indicated in this specification, individually or collectively, and any and all combinations of any two or more of the steps or features.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention claimed is:
1. A compound of formula (I)

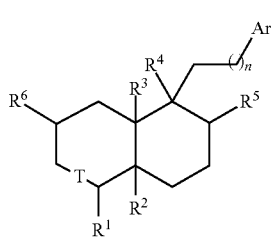

or a pharmaceutically acceptable salt or an ester prodrug thereof, wherein:
T is a double bond;
$R^1$ is selected from the group consisting of: $COOR^7$, $CONR^7R^8$, $COSR^7$, $COR^7$, $SO_3H$, $SO_2NR^7R^8$, $SO_2R^7$, $SONR^7R^8$, and $SOR^7$;
$R^2$, $R^3$, and $R^4$ are each independently selected from the group consisting of: H, optionally substituted C1-C12 alkyl, and optionally substituted C2-C12 alkenyl;
$R^5$ and $R^6$ are each independently selected from the group consisting of: H, OH, optionally substituted C1-C12 alkyl, =O, $(CH_2)mOC(O)R^9$, C1-C12 oxyalkyl, C1-C12 alkyloxy, C2-C12 oxyalkenyl, and C2-C12 alkenyloxy, provided at least one of $R^5$ and $R^6$ is $(CH_2)mOC(O)R^9$;
$R^7$ and $R^8$ are each independently selected from the group consisting of: H, optionally substituted C1-C12 alkyl, optionally substituted C2-C12 alkenyl, optionally substituted C2-C12 alkynyl, optionally substituted C1-C10 heteroalkyl, optionally substituted C3-C12 cycloalkyl, optionally substituted C3-C12 cycloalkenyl, optionally substituted C1-C12 heterocycloalkyl, optionally substituted C1-C12 heterocycloalkenyl, optionally substituted C6-C18 aryl, and optionally substituted C1-C18 heteroaryl;
$R^9$ is phenyl;
Ar is an optionally substituted aryl group; and
m and n are integers each of which is selected from the group consisting of 0, 1, 2, 3, and 4.
2. The compound of claim 1, wherein only one of $R^5$ and $R^6$ is $(CH_2)mOC(O)R^9$.
3. The compound of claim 1, wherein Ar is selected from the group consisting of: optionally substituted furan, optionally substituted thiophene, optionally substituted pyrrole, optionally substituted phenyl, and optionally substituted pyridine.
4. The compound of claim 3, wherein Ar is furan.
5. The compound of claim 1, wherein $R^1$ is $COOR^7$.
6. The compound of claim 1, wherein $R^2$ is methyl.
7. The compound of claim 1, wherein $R^3$ is H.
8. The compound of claim 1, wherein $R^4$ is optionally substituted C1-C12 alkyl.
9. The compound of claim 8, wherein $R^4$ is methyl.
10. The compound of claim 1, wherein $R^5$ is $(CH_2)mOC(O)R^9$ and $R^6$ is selected from the group consisting of H and OH.
11. The compound of claim 1, wherein $R^6$ is $(CH_2)mOC(O)R^9$ and $R^5$ is optionally substituted C1-C12 alkyl.
12. A compound selected from the group consisting of:

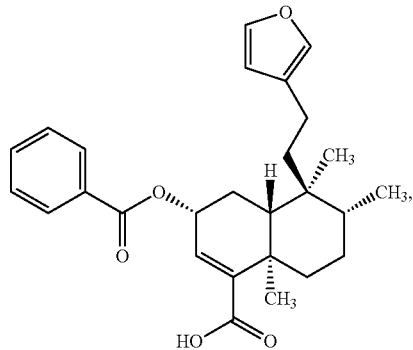

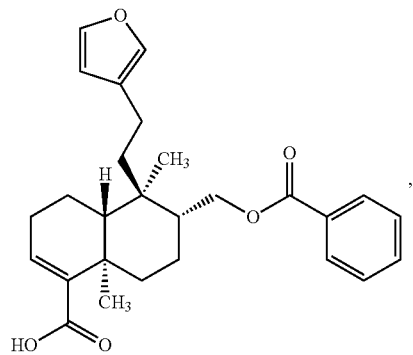

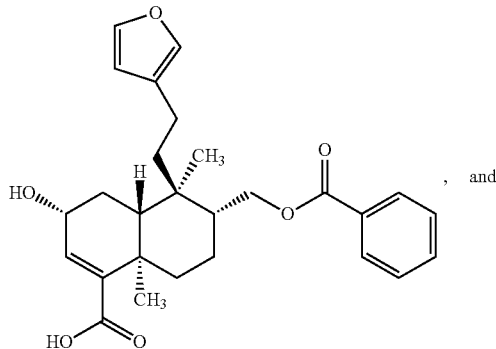

, and

-continued

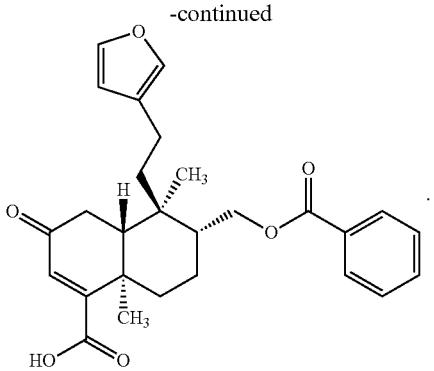

5

13. An anti-inflammatory *Dodonaea polyandra* extract comprising a compound of claim 1.

14. The anti-inflammatory extract of claim 13, wherein the extract comprises a benzoyl ester clerodane diterpenoid.

15. A composition comprising a compound according to claim 1 and a pharmaceutically acceptable carrier.

16. A method of treating inflammation in a subject, the method comprising administering to the subject a therapeutically effective amount of a compound according to claim 1.

17. A method of treating inflammation, the method comprising administering to a subject in need of such treatment a therapeutically effective amount of an extract according to claim 13.

* * * * *